(12) United States Patent
Just et al.

(10) Patent No.: US 7,311,670 B2
(45) Date of Patent: Dec. 25, 2007

(54) BLOOD PRESSURE CUFFS WITH RESILIENT SUPPORT SLEEVES

(75) Inventors: Steven Just, Raleigh, NC (US); David Gallick, Cary, NC (US); Dayn McBee, Cary, NC (US)

(73) Assignee: SunTech Medical, Inc., Morrisville, NC (US)

( * ) Notice: Subject to any disclaimer, the term of this patent is extended or adjusted under 35 U.S.C. 154(b) by 633 days.

(21) Appl. No.: 10/705,364

(22) Filed: Nov. 10, 2003

(65) Prior Publication Data

US 2004/0097816 A1 May 20, 2004

Related U.S. Application Data

(63) Continuation-in-part of application No. 10/292,174, filed on Nov. 12, 2002, now Pat. No. 6,988,992.

(51) Int. Cl.
*A61B 5/02* (2006.01)

(52) U.S. Cl. ............. 600/499; 600/485; 600/490; 600/495

(58) Field of Classification Search ............. 600/499; 606/202
See application file for complete search history.

(56) References Cited

U.S. PATENT DOCUMENTS

| | | | | |
|---|---|---|---|---|
| 3,669,096 A * | 6/1972 | Hurwitz | ............ | 600/499 |
| 3,757,772 A | 9/1973 | Goldblat et al. | ............ | 128/2.05 G |
| 3,892,425 A * | 7/1975 | Sakairi et al. | ............ | 280/743.1 |
| 4,007,734 A * | 2/1977 | Peters | ............ | 600/490 |
| 4,033,337 A * | 7/1977 | Raczkowski | ............ | 600/499 |
| 4,058,117 A * | 11/1977 | Kaspari et al. | ............ | 600/495 |
| 4,274,158 A * | 6/1981 | Pogorski et al. | ............ | 2/2.16 |
| 4,548,249 A * | 10/1985 | Slaughterbeck | ............ | 206/363 |
| 4,617,937 A * | 10/1986 | Peel et al. | ............ | 600/493 |
| 4,838,276 A * | 6/1989 | Nagai et al. | ............ | 600/499 |
| 4,967,758 A * | 11/1990 | Masciarotte | ............ | 600/499 |
| 4,979,953 A * | 12/1990 | Spence | ............ | 606/202 |
| 5,007,112 A * | 4/1991 | Lewis et al. | ............ | 2/457 |
| 5,251,646 A | 10/1993 | Bowen | ............ | 128/878 |
| 5,335,679 A * | 8/1994 | Baxter | ............ | 132/270 |
| 5,344,406 A * | 9/1994 | Spooner | ............ | 604/179 |
| 5,492,129 A * | 2/1996 | Greenberger | ............ | 600/528 |
| 5,511,552 A * | 4/1996 | Johnson | ............ | 600/499 |
| 5,513,643 A * | 5/1996 | Suite | ............ | 600/499 |
| 5,560,365 A | 10/1996 | Ogura | | |
| 5,626,142 A * | 5/1997 | Marks | ............ | 600/499 |

(Continued)

OTHER PUBLICATIONS

PCT International Search Report, International Application No. PCT/US03/35228 filed Nov. 3, 2003; mailed Jun. 18, 2004.

*Primary Examiner*—Charles A. Marmor, II
*Assistant Examiner*—Patricia C Mallari
(74) *Attorney, Agent, or Firm*—Myers Bigel Sibley & Sajovec PA

(57) ABSTRACT

Inflatable blood pressure cuff assemblies include an inflatable elongate cuff member having opposing long edges and opposing short edge portions with a fluid chamber therein and a resilient support sleeve with at least one rib support member, the sleeve attached to a respective one of the opposing short edge portions of the inflatable elongate cuff member. The sleeve may be configured with a sensor chamber and a cable routing channel. Related systems and methods of fabricating cuff assemblies and resilient support sleeves are also described.

56 Claims, 19 Drawing Sheets

U.S. PATENT DOCUMENTS

| | | |
|---|---|---|
| 5,660,182 A | 8/1997 | Kuroshaki et al. |
| 5,669,390 A * | 9/1997 | McCormick et al. ....... 600/499 |
| 5,746,213 A | 5/1998 | Marks ........................ 128/686 |
| 5,797,851 A * | 8/1998 | Byrd .......................... 600/499 |
| 6,036,718 A | 3/2000 | Ledford et al. |
| 6,171,254 B1 * | 1/2001 | Skelton ...................... 600/490 |
| 6,245,023 B1 | 6/2001 | Clemmons .................. 600/499 |
| 6,364,843 B1 * | 4/2002 | Lightle ....................... 600/490 |
| 6,478,745 B2 | 11/2002 | Nakagawa et al. ......... 600/499 |
| 6,525,238 B2 * | 2/2003 | Corrales ...................... 602/41 |

* cited by examiner

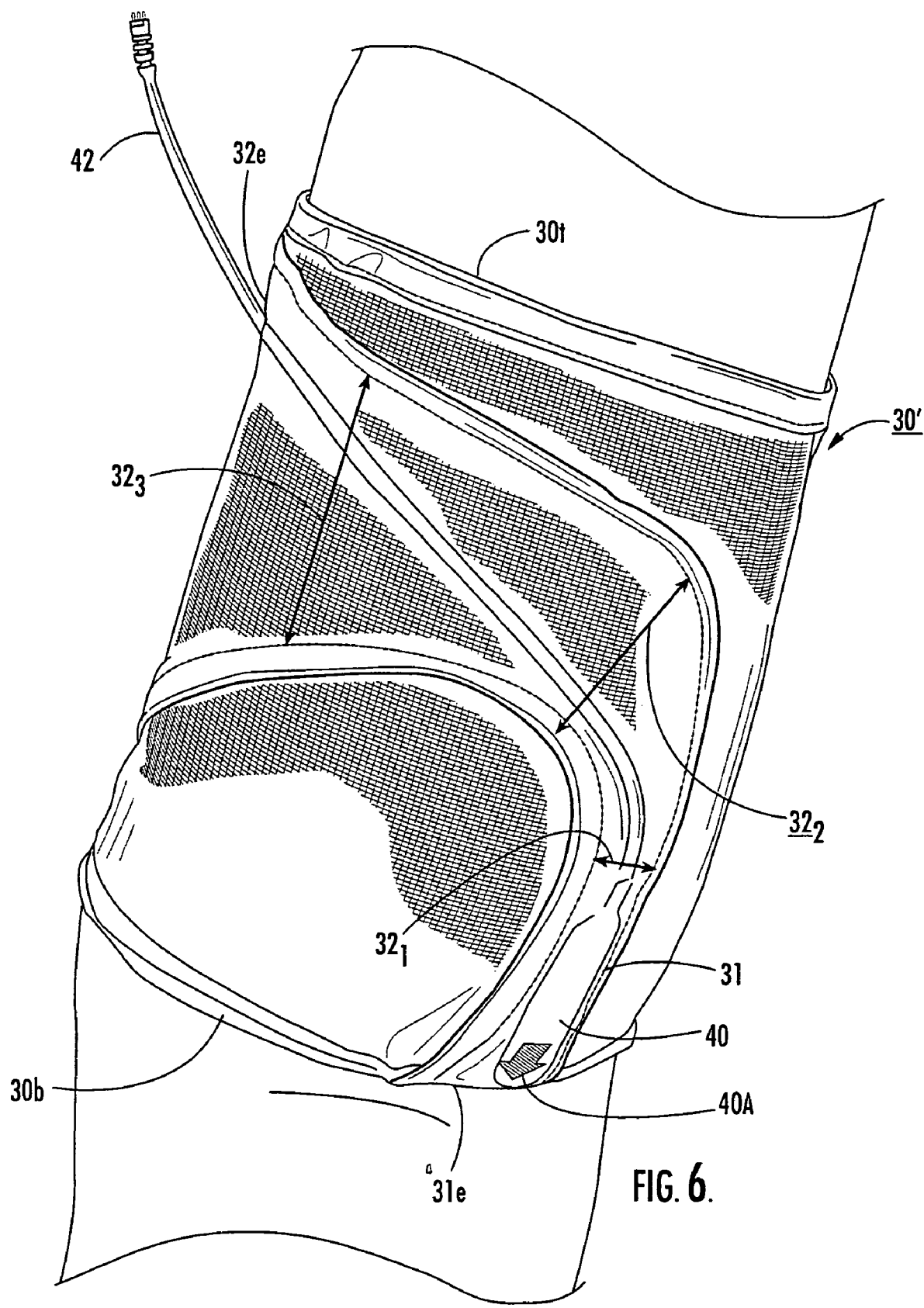

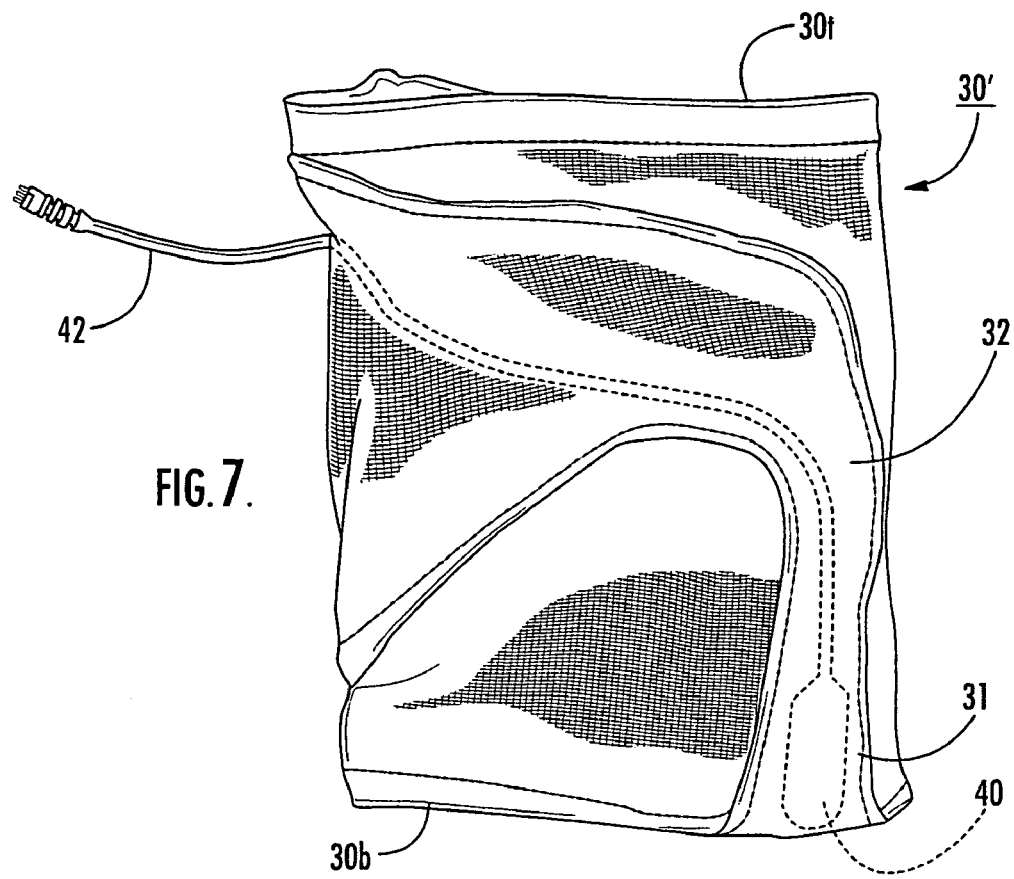
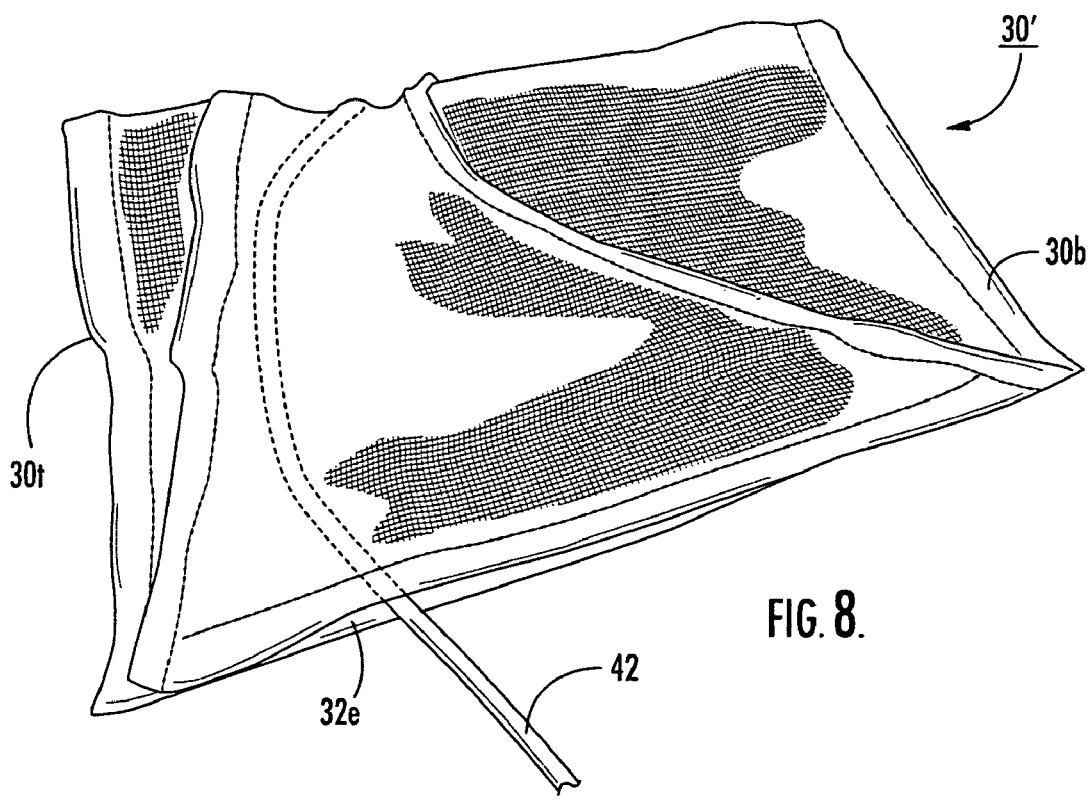

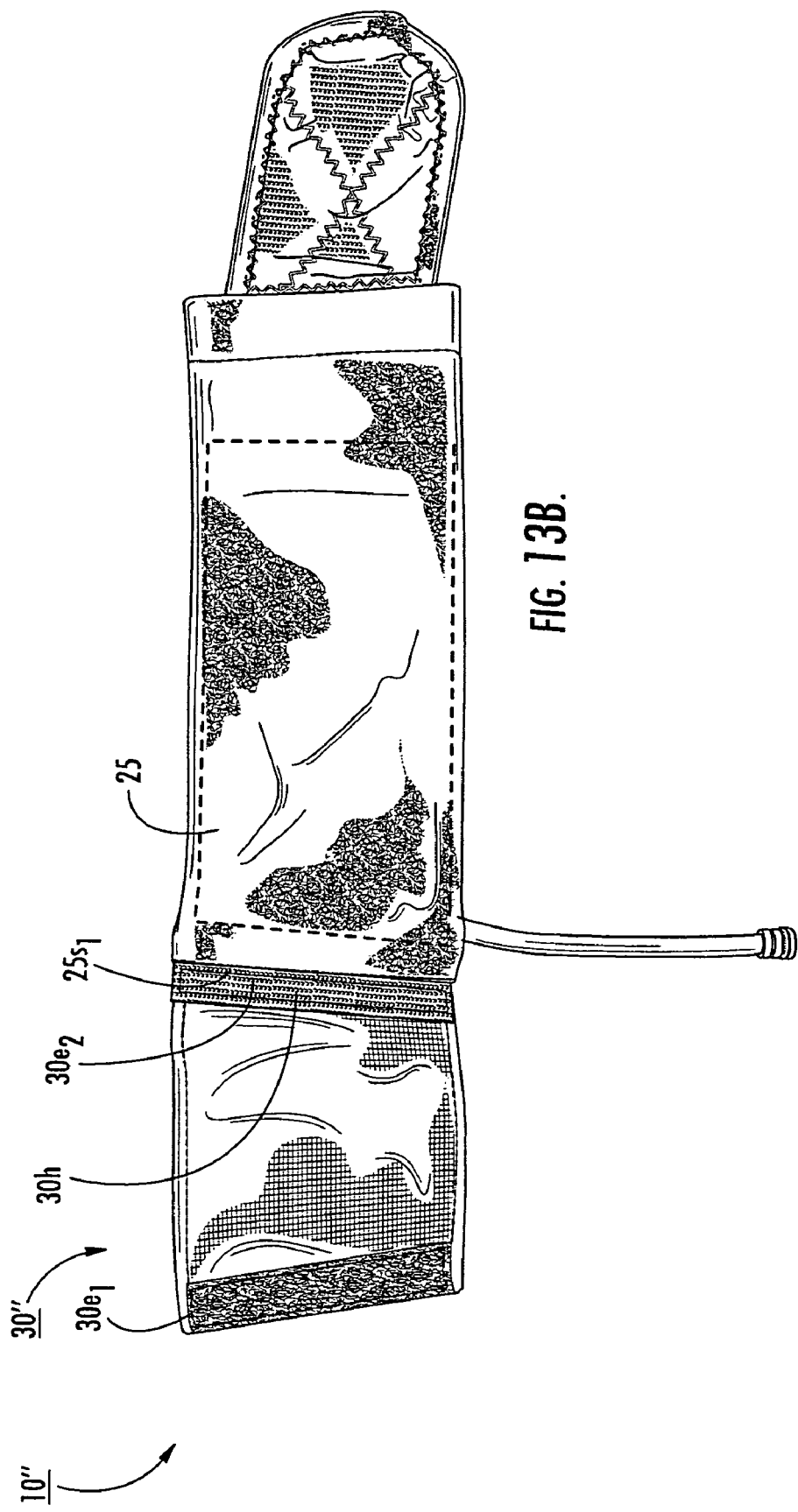

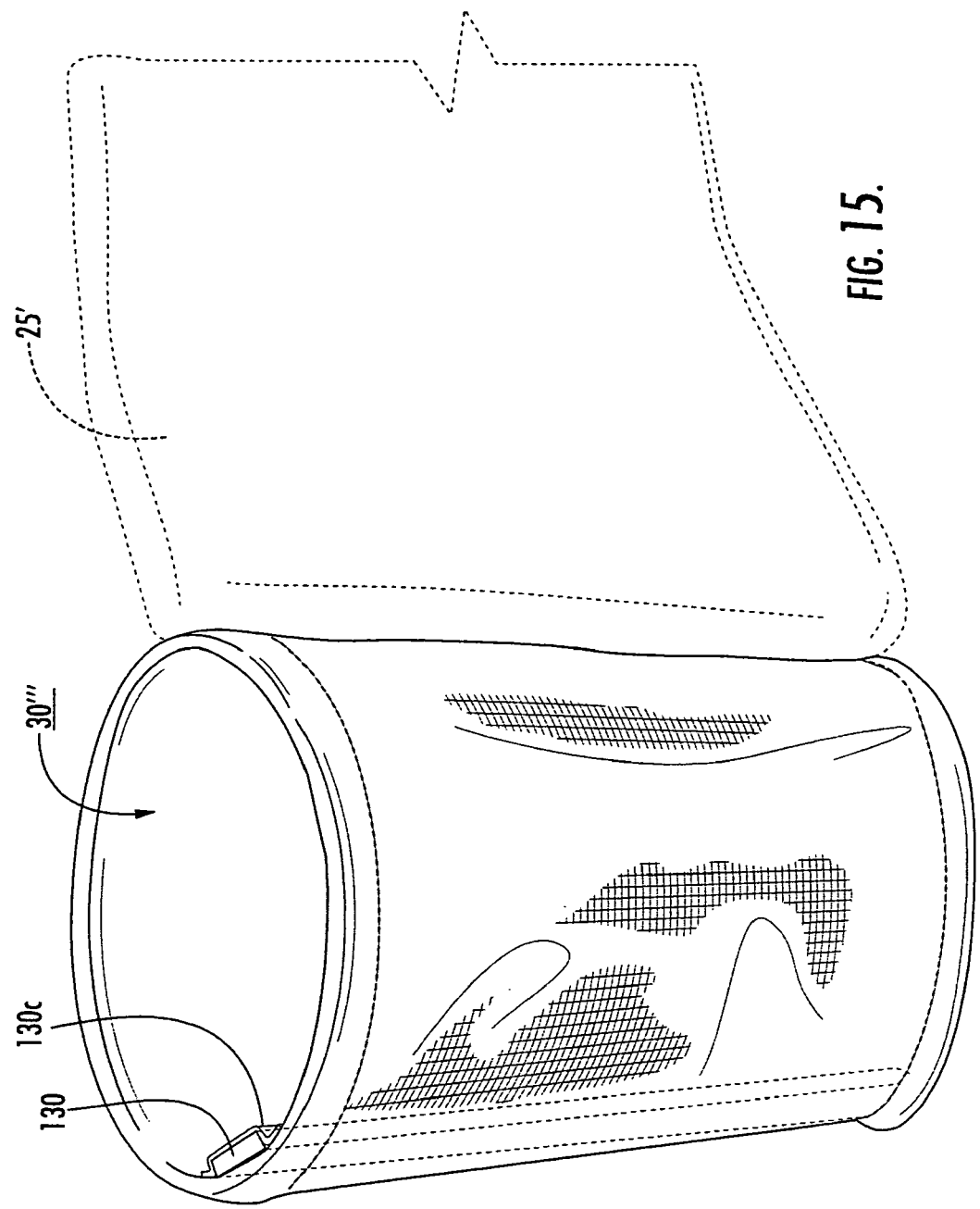

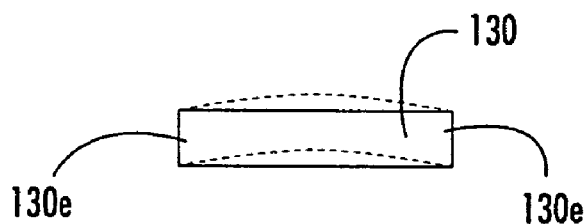
FIG. 16A.  FIG. 16B.
FIG. 17A.  FIG. 17B.
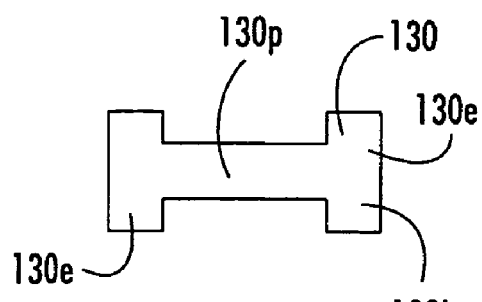
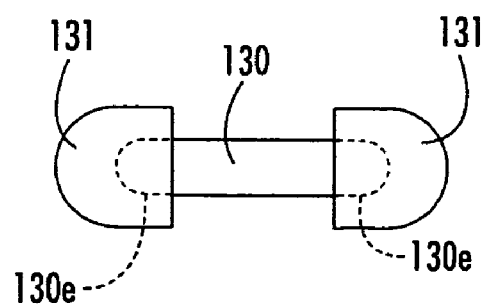
FIG. 17C.  FIG. 17D.

BLOOD PRESSURE CUFFS WITH RESILIENT SUPPORT SLEEVES

RELATED APPLICATIONS

This application is a continuation-in-part of U.S. patent application Ser. No. 10/292,174 filed Nov. 12, 2002, now U.S. Pat. No. 6,988,992, the contents of which are hereby incorporated by reference as if recited in full herein.

FIELD OF THE INVENTION

The present invention relates to blood pressure monitors and associated inflatable cuffs.

BACKGROUND OF THE INVENTION

Blood pressure monitoring systems may be ambulatory or stationary. The systems employ inflatable blood pressure cuffs to obtain blood pressure measurements of patients. In operation, the blood pressure cuff is typically wrapped around a limb (typically the arm) of a patient. The blood pressure cuff is inflated to provide a certain amount of pressure on a major artery in the limb (such as the brachial artery in the arm) so as to restrict the blood flow in the artery; then the pressure is slowly released until a measurement of the systolic/diastolic pressures are obtained.

Conventional blood pressure measurement devices include those that employ a mercurial manometer with a stethoscope and those that use a sensor to detect a Korotkoff sound to determine systolic and diastolic blood pressure of the patient. Thus, the pressure readings can be determined manually by a clinician that uses a stethoscope to listen for blood flow in the artery while the cuff is slowly deflated, or the pressure readings can be obtained in an automated manner without the use of a clinician by detecting the Korotkoff sound produced from an arterial vessel of the body portion being compressed by the blood pressure cuff. One example of an automated blood pressure monitoring system that can be used during stress testing or evaluation is the Tango™ System, available from SunTech Medical Instruments, Inc., Raleigh, N.C. Other proposed automated systems are described in U.S. Pat. No. 5,660,182 to Kuroshaki et al. and U.S. Pat. No. 5,560,365 to Ogura, the contents of which are hereby incorporated by reference as if recited in full herein.

Various blood pressure cuffs have been proposed in the past. For example, the blood pressure cuffs may be bladderless, such as that proposed in U.S. Pat. No. 6,036,718 to Ledford et al., or may be configured with an internal integrated bladder as described in U.S. Pat. No. 6,245,023 to Clemmons. The contents of these patents are hereby incorporated by reference as if recited in full herein. In use, particularly for automated systems, the blood pressure cuff should be wrapped on the subject so that the sensor used to obtain the blood pressure readings is properly positioned on the patient in the appropriate location to provide adequate signal and inhibited from slipping during the evaluation.

In the past, sensors (typically microphones) of the automated systems have been positioned in a pouch located in an internal primary surface of the cuff. However, the cable that connects the sensor to the external monitoring device may move or the sensor itself may not be held in reliably snug abutment to the skin and/or over the artery of interest. In other known devices, the sensor may be adhesively positioned directly onto the skin of the patient.

Despite the blood pressure devices noted above, there remains a need to provide improved blood pressure cuffs that can be comfortably positioned on a patient and, in certain embodiments, position the sensor proximate the artery of interest and/or in a manner that can improve the signal to noise ratio in the signal(s).

SUMMARY OF EMBODIMENTS OF THE INVENTION

Certain embodiments of the present invention provide blood pressure cuffs with resilient expandable support sleeves attached to the elongated cuff. Related systems and methods for obtaining blood pressure measurements as well as methods of fabricating blood pressure cuffs and/or sleeves are also described.

In certain embodiments, the sleeve can be configured as a resilient breathable fabric in a truncated cone configuration (i.e., "frustoconical" shape). The sleeve can be fabricated to provide stretch in the lateral direction sufficient to support the positioning of the blood pressure cuff on the desired limb. In certain embodiments, the stretch may be a two-way elasticity or stretch, with stretch in the lateral direction being greater than in the longitudinal direction. The sleeve can be attached to an end portion of the elongated cuff. The sleeve attachment may be integrally attached or fixed to the cuff body (for use over a number of patients) or detachable from the cuff body. In certain particular embodiments, the sleeve can be a single-use disposable member.

In certain embodiments, the sleeve may be configured with a rib support member and a sensor-holding chamber. The sensor-holding chamber can hold one or more sensors in a desired orientation and/or position relative to the patient during use. The sensor-holding chamber may be in communication with a curvilinear sensor-holding channel that can be sized and configured to receive, route, and support an associated sensor cable therein. The sensor-holding channel can be curvilinear and configured to provide strain relief support for the cable and/or inhibit sensor movement, which, in turn, can improve the SNR of the monitored signal.

Certain embodiments of the present invention are directed to an inflatable blood pressure cuff assembly. The assembly includes an inflatable elongate cuff member having opposing long edges and opposing short edge portions with a fluid chamber therein and a resilient sleeve attached to a respective one of the opposing short edge portions of the inflatable elongate cuff member.

Other aspects are directed to resilient support sleeves with externally held biosensors. The sleeves include: (a) a sleeve body having a sensor chamber and curvilinear sensor channel disposed intermediate opposing primary surfaces of the sleeve body for positioning a sensor and associated cabling therein and also having at least one rib support member.

The sleeve may include a sensor having a cable associated therewith, the sensor held in the sleeve sensor chamber and the sensor cable held in the sensor channel. The sensor is adapted to take a biophysical measurement of a patient during use and the sleeve body has a closed perimeter configuration defining an aperture extending in the axial direction. The sleeve aperture is sized and configured to laterally stretch to receive a predetermined anatomical body extremity, digit, or limb of a patient therein, during use, and the sleeve aperture has a first configuration with a first width during periods of non-use and a second configuration with an expanded second width when in position on a patient. When in the second configuration, the sleeve is substantially conformable to and resides securely against a desired portion of the extremity, digit, or limb of the patient with sufficient compressive force so that it is able to maintain its desired longitudinal position and hold the sensor in a desired location against the patient to thereby inhibit slippage during use.

Still other aspects are directed to methods of obtaining a blood pressure measurement in a patient. The method includes: (a) slipping a resilient sleeve attached to an inflatable blood pressure cuff onto a patient so that it resides on a selected body portion and stretches to compress the selected body portion; (b) wrapping the blood pressure cuff about the sleeve and attaching the cuff theretogether; (c) inflating the blood pressure cuff to a pressure sufficient to restrict blood flow in a selected artery proximate the sleeve and blood pressure cuff; (d) releasing the inflation pressure in the blood pressure cuff; and (e) detecting a signal in the patient corresponding to blood pressure measurements.

Additional aspects include automated blood pressure monitoring systems. The systems include: (a) a plurality of inflatable blood pressure cuff assemblies, each sized and configured to accommodate a different patient size range, each cuff assembly comprising an elongate cuff member having opposing long edges and opposing short edge portions with an inflatable fluid chamber therein and a resilient sleeve having a predetermined patient size range that is attached to a respective one of the opposing short edge portions of the inflatable elongate cuff member, the sleeve can have at least one rib support member; (b) means for inflating the desired blood pressure cuff to a pressure sufficient to restrict blood flow in a selected artery of a patient proximate the sleeve and the blood pressure cuff; (c) means for releasing the inflation pressure in the blood pressure cuff; and (d) means for detecting a signal corresponding to blood pressure measurements of the patient.

These and other objects and aspects of the present invention are explained in detail in the specification set forth below.

BRIEF DESCRIPTION OF THE DRAWINGS

FIG. 6 is an enlarged front view of a sleeve positioned on a patient according to embodiments of the present invention.

FIG. 7 is a front view of the sleeve shown in FIG. 6 in isolation of the patient.

FIG. 8 is a top view of the sleeve shown in FIG. 7.

FIG. 13B is a front view of a cuff assembly having a sleeve that can be releaseably attached in situ on the patient according to embodiments of the present invention.

FIG. 15 is a perspective view of a cuff assembly having a sleeve member with an alternatively configured rib support according to embodiments of the present invention.

FIGS. 16A and 16B are side views of an exemplary rib support illustrating a flexible configuration according to embodiments of the present invention.

FIGS. 17A and 17B are top views of exemplary rib support configurations according to embodiments of the present invention.

FIGS. 17C and 17D are side views of exemplary rib support configurations according to yet other embodiments of the present invention.

DESCRIPTION OF EMBODIMENTS OF THE INVENTION

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the claims unless specifically indicated otherwise.

The present invention is particularly suitable for monitoring biophysical responses in humans (adults and children) for medical evaluations. However, the present invention may also find use for monitoring biophysical responses in animals, fowl, reptiles, or other creatures, as well as for use in veterinarian applications, clinical trials, drug discovery programs and the like. In certain embodiments, the methods, devices, and systems of the present invention are primarily directed to assessing blood pressure measurements as the biophysical response of interest. The blood pressure measurements may be taken in a stationary and/or ambulatory system while the patient is at rest, experiencing normal life activities, undergoing stressful activity (whether by a certain elected physical recreational or work-related activity), or undergoing a medically-rendered stress test (chemically or physically induced). The blood pressure measurements may be obtained manually or in an automated manner whether via a mercurial or pneumatic manometer or by detection the Korotkoff sound or other desired detectable bio-parameter.

Figure 1:
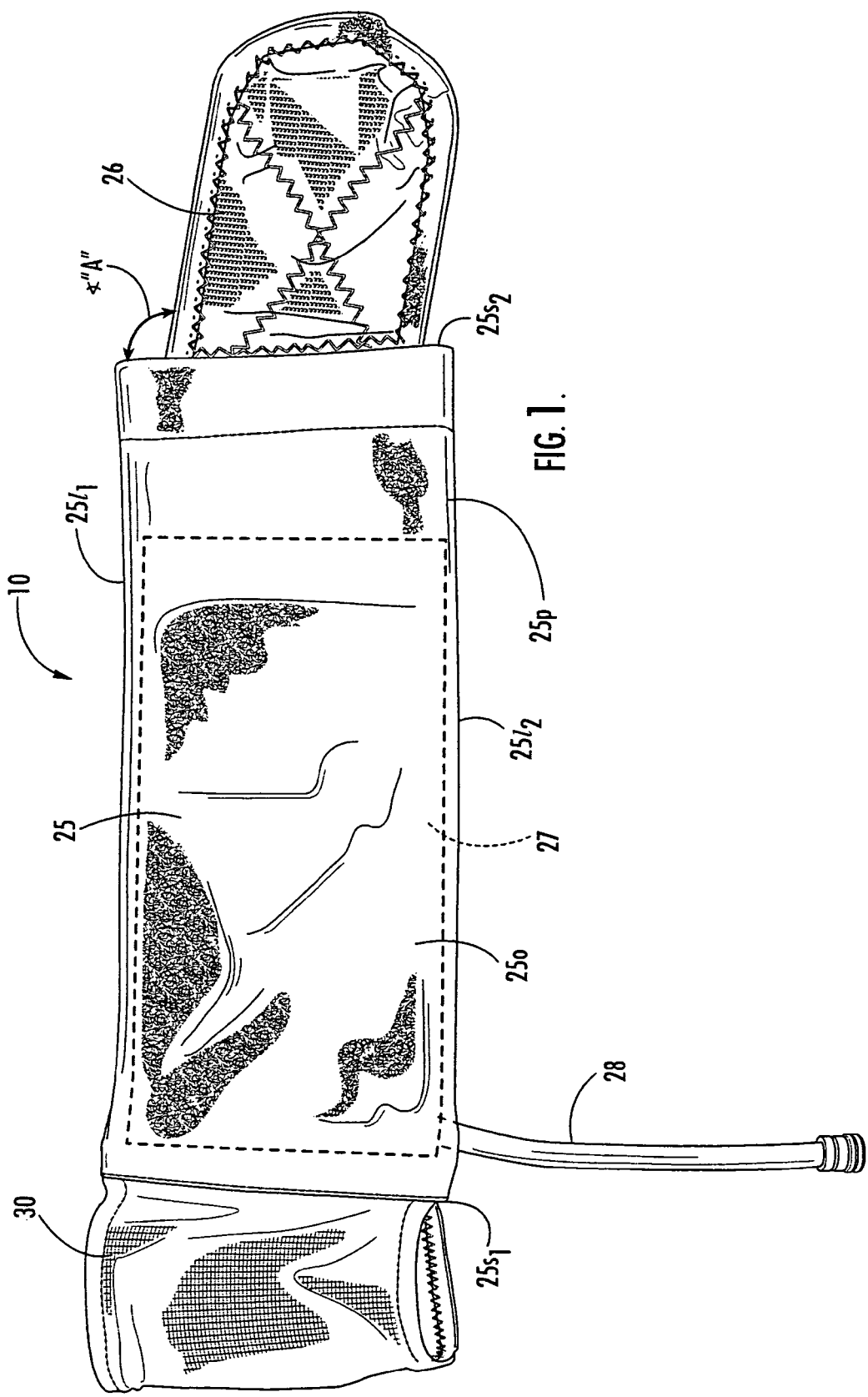
FIG. 1 is a front view of a blood pressure cuff assembly with a sleeve according to embodiments of the present invention.

Turning now to FIG. 1, one embodiment of a blood pressure cuff assembly 10 is shown. As shown, the cuff assembly 10 includes an elongated blood pressure cuff member 25, a resilient sleeve 30, and a tail portion 26 that is releaseably attachable to the cuff member body 25 to help in holding the cuff assembly 10 in position on a patient. The elongated blood pressure cuff member 25 is shown as including a pouch 25p and a separate inflatable bladder 27 with an associated fluid inflation tube 28. However, it is noted that, in other embodiments, the inflatable blood pressure cuff member 25 may be bladderless or include differently configured bladders, such as a plurality of discrete or concurrently inflatable bladders or bladder strips and the like.

The elongated cuff member 25 includes opposing long edge portions $25l_1$, $25l_2$, and opposing short edge portions $25s_1$, $25s_2$. The sleeve 30 can be attached to a first one of the short edge portions 25s, with the tail portion 26 attached at the second short edge portion $25s_2$. The attachment can be secured by one or more of sewing, adhesively binding, heat bonding, and the like.

The inner primary surface 25i of the cuff member (FIG. 2) i.e., the surface that is positioned in intimate contact with the patient during use, can be formed of a material that can be resistant to absorption of biofluids and/or that is easily cleansed or sanitized between uses. One suitable material may be a polymer or copolymer, or blends and derivatives thereof, such as nylon or another biocompatible, substantially impermeable elastomeric material. The material may be coated with a suitable biocompatible coating layer such as polyurethane to provide the desired moisture repellant or resistance. In addition to, or alternatively, in certain embodiments a disposable cover layer may be positioned to overlie the inner primary surface to promote hygiene between patients (not shown).

The opposing (outer) primary surface 25o of the cuff member can be formed of a similar material or a different material. In the embodiment shown, the outer primary surface 25o includes at least a portion with VELCRO® loops that releaseably engage with VELCRO® hooks in the tail portion 26 of the cuff member 25 to make the attachment width-adjustable to accommodate various patient widths. Other fastening members or components may also be employed to provide the releaseable size-adjustable attachment of the wrapped cuff member 25.

Figure 2:
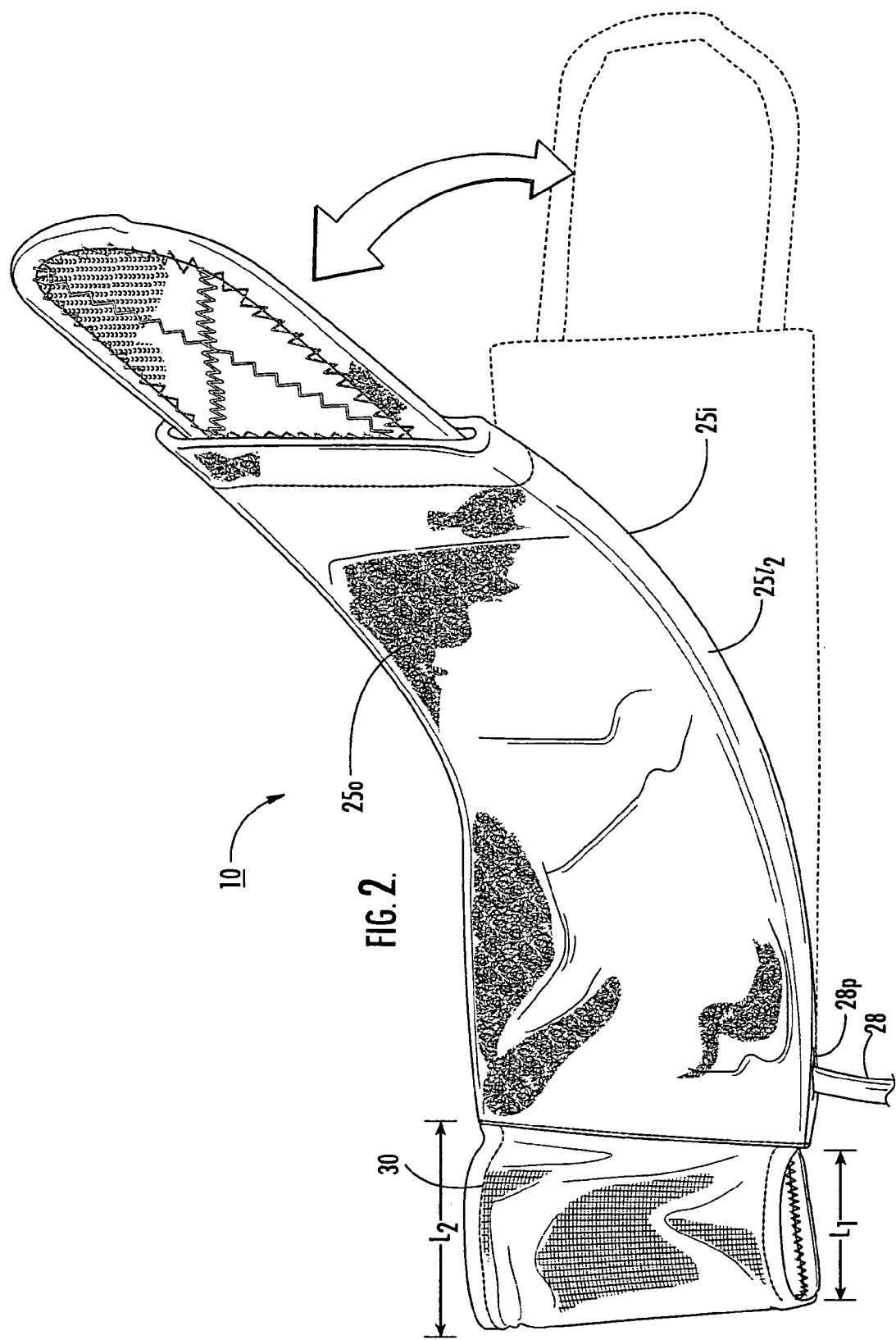
FIG. 2 is a front view of the blood pressure cuff assembly shown in FIG. 1, illustrating the cuff member being wrappable about the sleeve.

FIG. 2 illustrates that, in position, the cuff member 25 wraps about the sleeve 30 in an orientation that positions the inner primary surface against the sleeve 30. The cuff assembly 10 can be configured in size and shape to wrap around any desired body part, typically an extremity, limb or digit. In certain embodiments, the cuff assembly 10 is configured to take blood pressure measurements on an upper arm of a patient by detecting blood pressure sounds or responses in the brachial artery. In other embodiments, the cuff assembly 10 can be configured to take blood pressure measurements on a leg (typically an upper portion of the leg where measurements can be taken from the femoral artery). The cuff assembly 10 can be configured to be useable to obtain measurements from either the right or left arm (or leg) of the patient. The tube 28 may be configured to exit from the same location from the cuff member 25 irrespective of its use, or the cuff member 25 may be formed with alternative exit ports for easy alteration of the bladder positioning in the cuff member pouch 25 and/or the associated tube 28 exit selected.

FIG. 2 also illustrates that a port 28p can be formed along one of the long edges (shown as the bottom long edge $25l_2$) of the pouch 25 to allow the tube 28 to direct the inflation fluid medium into the inflatable cuff member 25 (shown as into the bladder 27 in the pouch 25p). The port 28p can be located in other locations on the inflatable cuff member 25 as appropriate so as not to interfere with the operation of the cuff assembly 10 or the attachment thereof. In addition, additional fluid inflation and/or pressure relief/exhaust lines may also be employed (not shown). The inflation medium is typically air but can be any suitable fluid (liquid or gas); the inflation fluid is typically chosen for its cost and safety (i.e., its non-toxicity or patient biocompatibility).

The sleeve 30 is resilient and sized and configured with elasticity sufficient to stretch to encase and reside snugly about and against the desired anatomical object held therein. The sleeve 30 can help to provide support for the cuff member 25 to hold it in position on the subject, supplementing the wrapped attachment of the cuff member 25 against itself to inhibit movement or slipping of the cuff member 25 away from the desired monitoring position. This support enhancement can be desirable during automated or long monitoring events or periods as well as when the cuff member 25 is to be worn by users during stress evaluations or dynamic monitoring applications.

The sleeve 30 can be fabricated to provide elasticity or stretch in the lateral direction sufficient to provide the desired support force to hold the sleeve 30 and/or the cuff member 25 in location on the limb or other location of the subject during use. In certain embodiments, the sleeve 30 can be configured with anisotropic (two-way) elasticity or stretch, so that the stretch in the lateral direction is generally greater than in the longitudinal direction.

The sleeve 30 can be formed of a breathable air-permeable fabric that inhibits sweat accumulation and can flex with the movement of the patient (flexure of the muscles thereunder and/or flexure attributed to movement of the arm, leg, and the like) so as to promote patient comfort. As such, the sleeve 30 can be configured with sufficient stretch to firmly reside on the patient while not imparting undue compression force onto the arm or other body part of the subject. In certain applications, the sleeve 30 may inhibit bruising or "pinching" of the skin and/or tissue of the user. For example, in certain patients, such as geriatric subjects, arms that have hanging or folds of skin and/or have reduced muscle definition may be subject to pinching when conventional cuff members are inflated and compress and encase, potentially trapping loose skin and pinching the user. In contrast, the sleeve 30 can be configured to encase the limb in a snug, tight, form-fitting conformable sleeve 30 that is functionally "molded" in situ to take the shape of the underlying limb of the user. Because the sleeve 30 encases the limb during use, it inhibits the occurrence of skin being trapped or pinched in the cuff member 25 as the bladder in the cuff is inflated. For example, in position, the sleeve 30 may be resiliently altered in shape from its non-use configuration into a substantially cylindrical (for substantially straight limb anatomical physiological structure) or into a substantially frusto-conical shape (for limbs that taper from larger to smaller cross-sectional widths top to bottom).

Suitable breathable fabrics include synthetic "stretch" or elastomeric fibers. An example of a stretch fiber is a synthetic manufactured fiber, such as spandex, in which the fiber forming substance is a long-chain synthetic polymer. As generally described in certain literature, it is believed that spandex typically comprises at least about 85% of a segmented-polyurethane. According to certain prior art sources, the polymer chain is a segmented block copolymer containing long, randomly coiled, liquid, soft segments that move to a more linear, lower entropy, structure. Generally stated, the hard segments act as "virtual cross-links" that tie all the polymer chains together into an infinite network. This network prevents the polymer chains from slipping past each other and taking on a permanent set or draw. When the stretching force is removed, the linear, low entropy, soft segments move back to the preferred randomly coiled, higher entropy state, causing the fiber to recover to its original shape and length. This segmented block copolymer is formed in a multi-step proprietary process. It is extruded into a fiber as a monofilament thread line or, for most products, into a multiplicity of fine filaments that are coalesced shortly after they are formed into a single thread line.

The synthetic stretch fibers can be stretched repeatedly and still recover to very near its original length and shape and have a stronger, more durable and higher retractive force than rubber while also being lightweight, soft, smooth, supple. The stretch fiber can be resistant to deterioration by body oils, perspiration, lotions or detergents and when fabrics containing spandex are sewn, the needle causes little or no damage from "needle cutting" compared to the older types of elastic materials. The synthetic stretch fiber is typically available in fiber diameters ranging from about 10 denier to 2500 denier.

LYCRA® is an example of a spandex stretch fiber. Other stretch fibers may also be suitable. For example, but not limited to, fibers presently classified in the polyester textile label classification of the U.S. Federal Trade Commission, but under which a new subclass of "elasterell-p" has been proposed, may also be a suitable stretch fiber as it is described as an inherently elastic, bicomponent textile fiber consisting of two substantially different forms of polyester fibers, and DuPont's version of this fiber is referred to as "T400."

The sleeve 30 may be formed of fabric one or more blends of stretch fibers such as nylon, spandex and/or LYCRA®. The one or more stretch fibers can be blended with host fibers that may also be synthetic or natural fibers. Thus, selected ones or blends of stretch fibers can be combined with other natural or synthetic fibers such as cotton, wool, silk, RAYON®, and the like.

One suitable sleeve 30 fabric is available from Elastic Fibers of America, located in Greensboro, N.C., identified as EFA style 5427, and comprises about 85% nylon and about 15% LYCRA® fibers in a 4.8 ounce/square yard fabric weight. In certain embodiments, during manufacturing, orientation indicia (not shown) may be applied to the sleeve material to facilitate proper assembly so that operators can orient the fabric to align the material with the maximum stretch direction of the material being configured in the lateral direction of the finished sleeve 30.

Figure 9A:
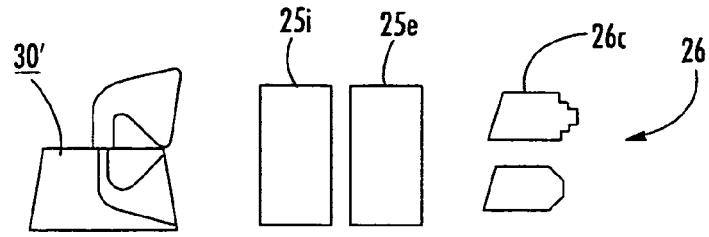
FIG. 9A is a schematic illustration of exemplary components that can be used to fabricate the cuff assembly with its sleeve according to embodiments of the present invention.
Figure 9B:
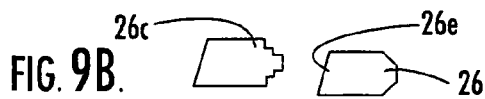
FIG. 9B illustrates the cuff tail portions (with hook and loop material) to form portions of the cuff member according to the components shown in FIG. 9A.
Figure 9C:
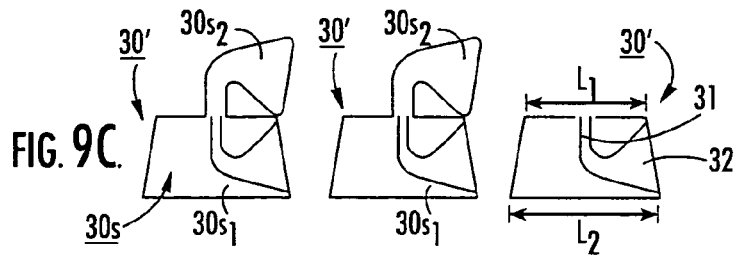
FIG. 9C illustrates an integral sheet configuration that can be used to form the sleeve in the components shown in FIG. 9A according to embodiments of the present invention.

In certain embodiments, the sleeve 30 can be configured in a resilient truncated cone configuration (i e., a "frusto-conical" shape), with the width at the upper portion $L_2$ (FIGS. 2, 9C) greater than the width at the lower portion $L_1$ (FIGS. 2, 9C). In other embodiments, the sleeve 30 can have a substantially cylindrical or other desired shape (not shown). Either sleeve configuration can be provided so that it can fit both straight and/or conical shaped limbs. In certain embodiments, the sleeve 30 can be provided in an array of sizes thereby allowing a clinician to select the size suitable for the patient (typically with a guide as to which sleeve fits different sizes of patients). In other embodiments, the cuff assemblies 10 themselves with associated sleeves 30 are provided in an array of sizes allowing snug fit of the sleeve 30 on the patient and sufficient length of the elongated cuff member 25 to provide the desired compression over the artery being used to obtain a reading. Suitable exemplary sizes will be discussed further below.

In particular embodiments, the sleeve 30 can be a disposable, single-use sleeve that is releasably attachable to the cuff member 25. In other embodiments, the sleeve 30 can be releaseably attached to and/or detached from the cuff member 25 at selected or each use, over a plurality of different patients (re-useable on subsequent patients).

In other embodiments, the sleeve 30 is integrally attached to the cuff member 25 so that each component remain fixed together during the life of the cuff assembly 10.

In addition, as shown in FIGS. 13A-13D, the sleeve 30" can be configured with a detachable edge portion that can be attached to enclose the region or limb after it is positioned at the desired location and before the cuff is wrapped together as will be discussed further below.

The lower and upper lengths, $L_1$ and $L_2$ of the sleeve 30, 30' (FIGS. 2, 9), 30" (FIGS. 13A-13C) can be established based on a minimum patient size so that $L_1$ is less than the corresponding size of the location on the body part of the patient in order to provide the desired compression force and support during use. For example, the lower length $L_1$ may be configured to be about 0.85 the minimum patient size (measured at the body location on the patient where the lower portion of the sleeve is to reside in use) while $L_2$ may be about the same or greater than the minimum patient size (such as about 1.05 times the patient width). The sleeve geometry and/or sizes can vary depending on the number of different size ranges of cuffs desired as well as the stretch capability of the sleeve. It is noted that the length features $L_1$ and $L_2$ can represent a dimension that is associated with the area of the outer perimeter and/or the width of the patient body part such as the circumference of the limb, at which the sleeve 30 will reside during use. In any event, the sleeve configuration can be selected so that it is undersized relative to the anatomical dimensional size of the patient to provide the desired snugness or conformal fit and/or compression.

In certain embodiments, the sleeve 30 can be configured with anisotropic (two-way) stretch so that it has an elastic lateral stretch that is greater than the longitudinal stretch. For example, but not limited to, a lateral stretch of at least about 50% at the lower edge portion of the sleeve 30 and at least about 10% elastic stretch in the longitudinal direction. The sleeve 30 can be configured to accommodate patients having limbs that vary in width by up to at least about 150%. The cuff assembly 10 can be provided in an array of different sizes (e.g., child, adult small, adult medium, adult large, adult extra large, adult extra-extra large and the like) with corresponding size adjustments to the sleeve 30 and cuff member 25. The sizes may be such that each is directed to the same anatomical location on a patient, or for different locations. For example, the adult XXL size may be configured for positioning on the thigh of an adult patient.

As noted above, the sleeve 30 can be configured so that it has an undersized width relative to the limb or body portion of the target patient (or patient group). By undersized, it is noted that the sleeve 30 will be forced to stretch to accommodate the patient(s) during use. In certain embodiments, the sleeve can be undersized by at least 10%. By configuring the sleeve 30 to be slightly undersized, on at least one side (upper and/or lower edge portions), the sleeve 30 can accommodate both substantially straight, and/or conically-shaped limbs or body portions.

For example, the sleeve 30 can be configured so that $L_1$ (the dimension at the lower portion of the sleeve 30 (FIGS. 2, 9C)) is at least 15% less than the width of the corresponding body part of the patient. For example, for a patient (child) minimum arm circumference or width about the brachial artery (above the elbow) of about 4.33 inches (11 cm), the length $L_1$ can be sized to be about 0.85 (4.33) or 3.68 inches. The sleeve 30 size can be configured with sufficient elasticity to fit patients having arm widths of up to about 50-225% or more, and more typically between about 100-205%, the rated size. For example for a rated "minimum size" of 4.33 inches, the (3.68 inch) sleeve 30 can be used for patients sized between about 4.33-8.88 inches. There can be some overlap in sizing (i.e., certain patients can use different standardized-sized cuff assemblies/sleeves). Examples of suitable sleeve sizing are given in Table 1.

TABLE 1

| Size | Size Descriptor | Arm/Leg Circumference Minimum inches (cm) |
|---|---|---|
| S | Child | 4.33 (11) |
| M | Small Adult | 7.09 (18) |
| L | Adult | 9.84 (25) |
| XL | Large Adult | 12.60 (32) |
| XXL | Adult Thigh | 15.75 (40) |

Figure 3:
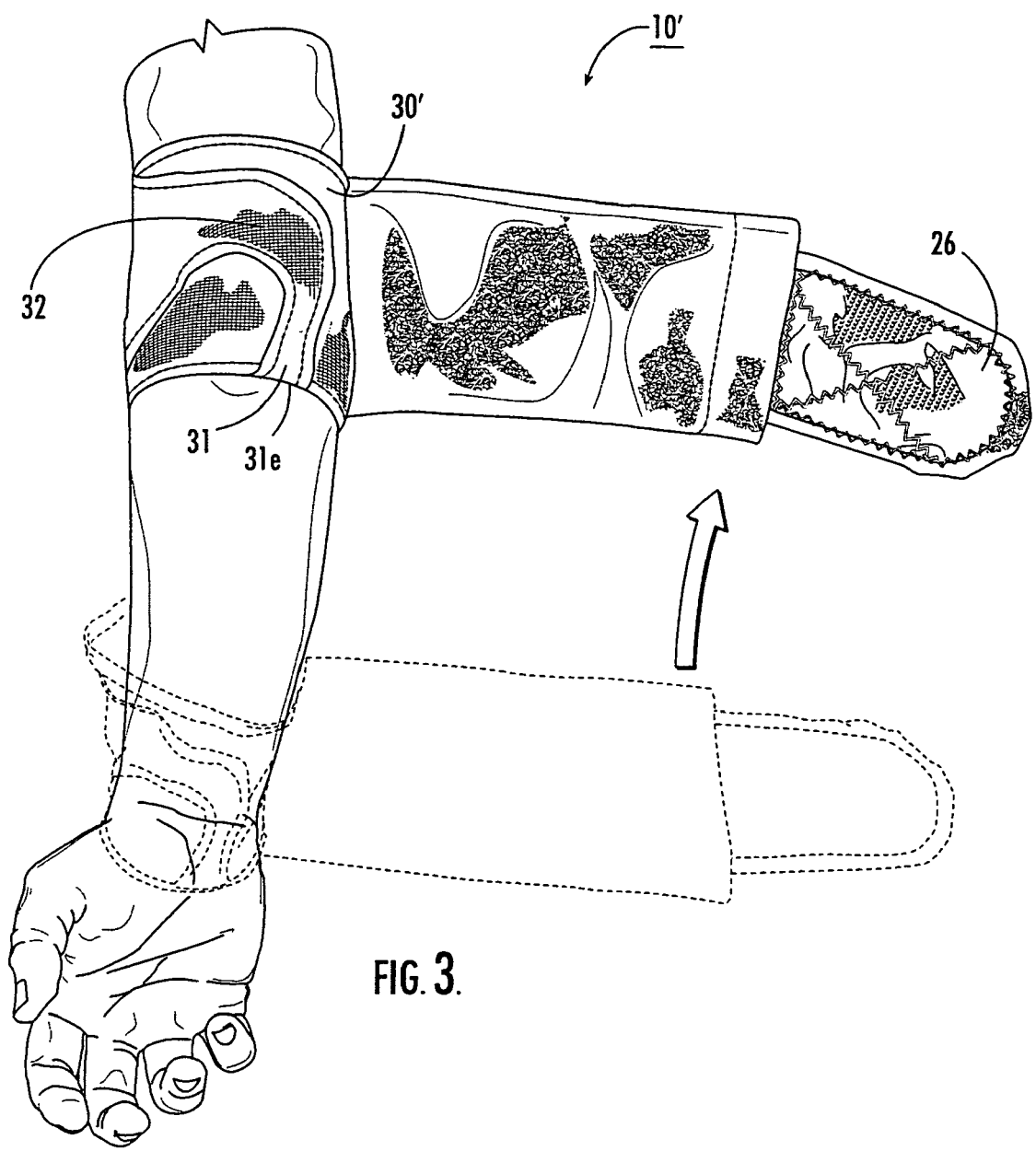
FIG. 3 is a front view of the blood pressure cuff assembly of FIG. 1 illustrating operations to position the cuff assembly on a patient according to embodiments of the present invention.
Figure 4:
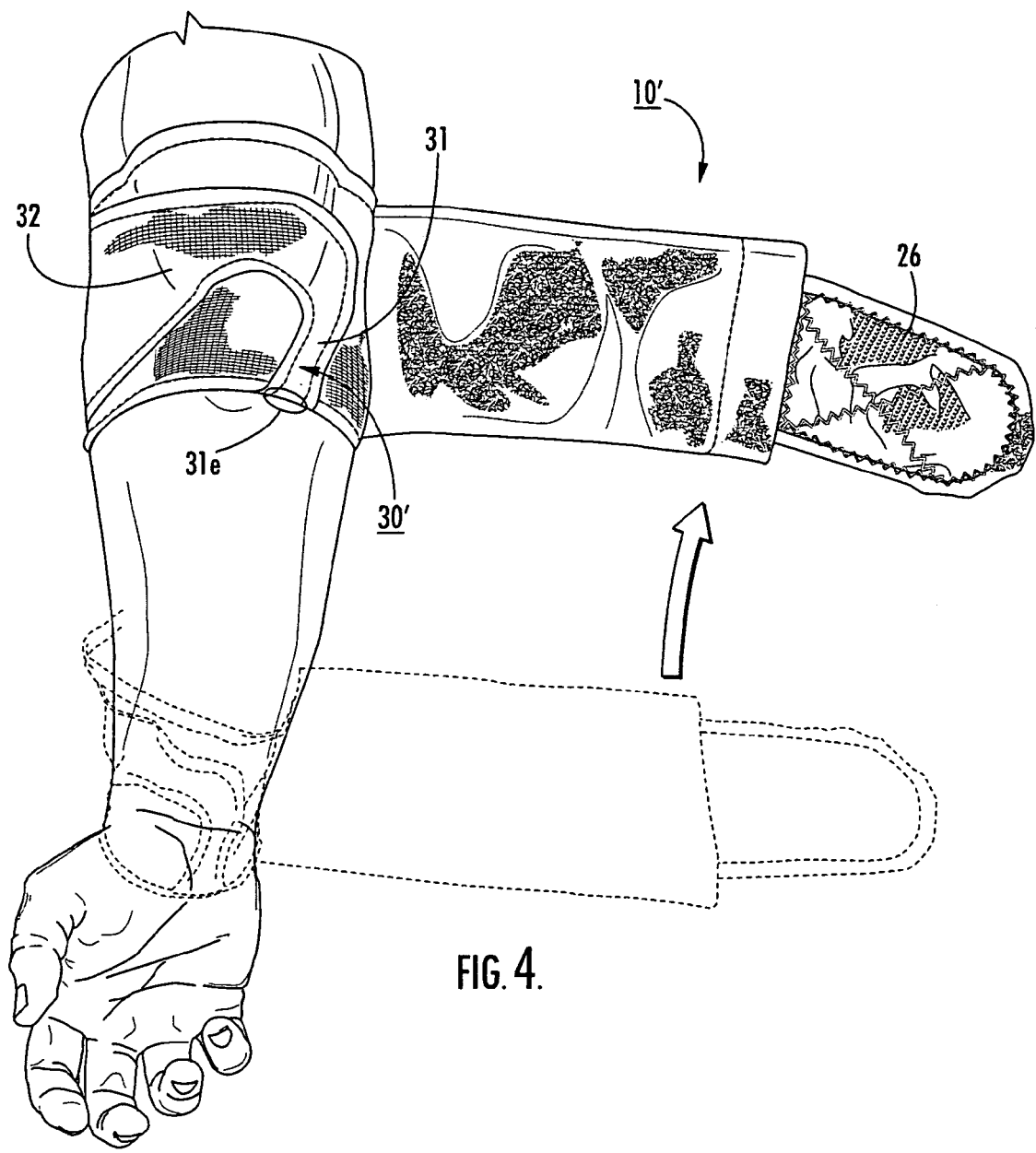
FIG. 4 is a front view of the blood pressure cuff shown in FIG. 3, but illustrating that the sleeve can be configured to snugly fit or accommodate differing anatomical sizes and shapes, according to embodiments of the present invention.
Figure 5:
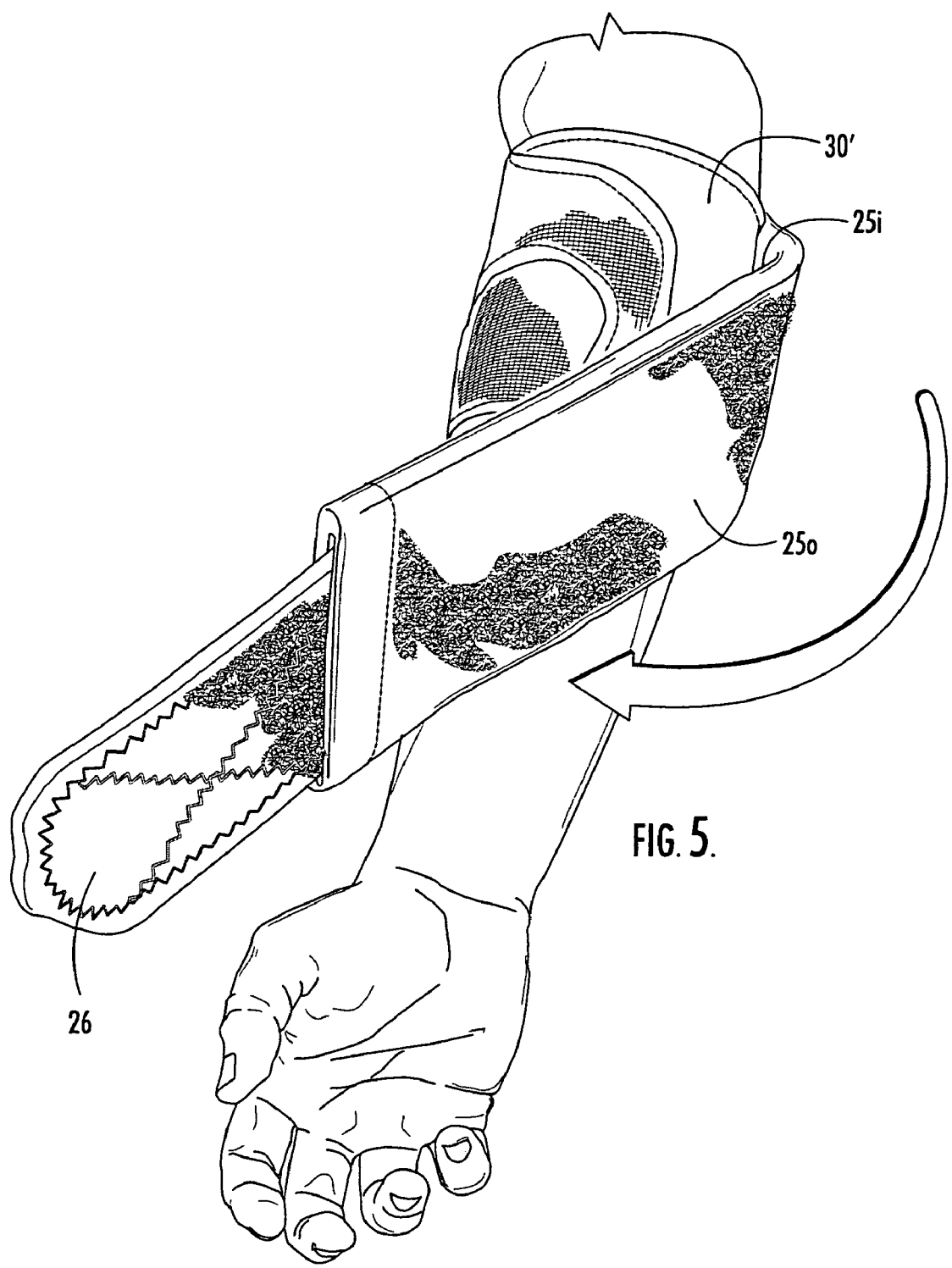
FIG. 5 is a front view of the cuff assembly shown in FIGS. 3 and 4 illustrating that the cuff member can be wrapped about the patient after the sleeve is suitably positioned thereon according to embodiments of the present invention.

FIG. 3 illustrates that the sleeve 30, 30' can be first slipped onto the body portion (shown as an arm) of the subject into a desired monitoring position, then the cuff member 25 can be wrapped about the arm (or other body part of interest) as shown in FIG. 5. FIG. 4 illustrates that the sleeve 30, 30' is configured to fit across ranges of patient sizes (the patient's arm is larger than the patient arm illustrated in FIG. 3) and provide the desired snug fit and suitable compression for support on each patient.

FIG. 3 also illustrates another embodiment of the cuff assembly 10'. In this embodiment, the sleeve 30' includes a sensor chamber 31 sized and configured to hold one or more sensors 40 (FIG. 6) in a desired orientation and/or position in the sleeve 30' relative to the patient during use. The sensor-holding chamber 31 may be in communication with a sensor channel 32 that can be sized and configured to receive, route, and support an associated sensor cable 42 therein (FIG. 6). The sensor channel 32 can be curvilinear and configured to provide strain relief support to inhibit bending of the cable and/or inhibit sensor movement, which, in turn, can improve the signal to noise ratio (SNR) of the monitored signal.

It is noted that the description of the sleeve, such as but not limited to, the size and/or materials for sleeve 30 as used herein can also apply to sleeve 30' and/or sleeve 30" throughout, unless noted otherwise.

As shown in FIG. 6, the sensor chamber 31 can be located at a bottom edge portion of the sleeve 30. The sensor chamber 31 may have a closed, downwardly-extending end portion 31e as shown in FIGS. 3 and 6, or an open-end portion 31e' as shown in FIG. 4. For the closed configuration of the end portion 31e, the lowermost edge portion may be seamless to allow the sleeve 30 and sensor 40 held in the sensor chamber 31 to be in skin-conformable snug abutment with the underlying body portion of the patient and thereby improve SNR and/or inhibit interference with signal monitoring during use.

As shown in FIG. 6, the sensor channel 32 may be configured to direct the cable 42 to veer from a substantially longitudinal orientation at the lowermost portion of the channel 32 to an orientation that includes components in the lateral direction as the cable 42 exits out of the channel exit port 32e at a top portion of the sleeve 30'. As such, the channel 32 may include, in serial order, described from the bottom 30b to the top of the sleeve 30t, a first substantially longitudinal upwardly extending segment $32_1$, an arcuate intermediate segment $32_2$, and a third substantially lateral segment $32_3$. The channel 32 can be configured with increasing width from top to bottom of the sleeve 30'. The channel 32 can have other configurations and the exit port 32e may be at other locations.

Examples of suitable sensors 40 include, but are not limited to, transducers, microphones, ceramic bimorphs, piezoelectric materials, including piezoelectric ceramics and/or polymers, and the like. Suitable sensors identified as Part nos. 98-0006-00, 9-0006-01, 91-0051-00; and 91-0051-01 are available from SunTech Medical Instruments, Inc., located in Raleigh, N.C.

During operation, the resilient sleeve 30 can act to at least partially decouple the sensor 40 from motion inherent in normal bladder inflation and deflation of the cuff member 25. The sleeve 30 can reduce noise and aid in stabilizing the sensor 40 against the user. That is, unlike certain conventional cuffs, the sleeve 30 inhibits sensor 40 movement away from the user, even during inflation of the bladder or chronic (ambulatory use). In addition, the resilient sleeve 30 may act as a spring to provide vibration dampening of the components used to obtain the desired readings.

As shown in FIGS. 1-5, the sleeve 30 can be attached to one of the short edge portions (shown as $25s_1$) of the cuff member 25. As noted above, the sleeve 30 can be configured so that it is an integral part of the cuff member 25 (made to remain intact with the cuff member 25 over their normal use life and used for a plurality of different patients). In other embodiments, the sleeve 30 may be detachably configured to be a single use-disposable sleeve or to be able to be size-selected at the point of use and/or sterilized apart from the cuff member 25 between uses and reattached and reused. For the attached version, the sleeve 30 may be sewn to the cuff member 25, adhesively bonded, or otherwise securely attached in a non-detachable semi-permanent or permanent manner.

For the detachable version, the sleeve 30 may again use hook and loop material such as VELCRO® for engagement to the cuff member 25. Pivot connectors, such as hooks and loops, locking tabs, spring loaded tabs, bayonet locks, zippers, adhesives, curable resin materials, or other suitable attachment means and/or devices, may also be used to provide the releaseable attachment interface between the sleeve 30 and the cuff member 25. The releaseable attachment should be formed with sufficient strength so as to be able to withstand the weight of the cuff member 25 as the sleeve 30 is slidably advanced over the extremity, limb, or digit of the patient and exposed to inflation and deflation of the inflatable cuff member 25. As such, for adhesive, resin, or other temporary bonds, the peel strength may be reduced relative to the torsional or torque strength of the attachment strength.

The sleeve 30 can facilitate installation by eliminating the need for a "D-ring" connector as well as permitting one-hand installation. In addition, the sleeve 30 can inhibit the cuff member 25 from falling off the limb or sliding down the limb in ambulatory blood pressure (ABP) and/or stress testing applications (where more than one reading may be desired over a monitoring interval). For example, in ABP applications, a 12-24-hour monitoring period may be observed where the patient wears the cuff 10 for intermittent pressurization thereof. For conventional cuffs, repeated expansion and contraction of the cuff member 25 can loosen the cuff and allow the cuff member and/or the sensor to become incorrectly positioned or slip or fall from the limb (such as the arm). The sleeve 30 can reduce the likelihood that these operational difficulties will occur. The sleeve 30 can help keep the sensor 40 aligned with the desired arterial vessel and hold the senor 40 snugly against the limb or skin of the patient during inflation and/or deflation of the bladder.

In other embodiments, as shown in FIGS. 13A-13D, the sleeve 30" can be configured with at least one wrappable edge portion $30e_1$ that can be attached to either the other opposing edge portion of the sleeve $30e_2$ or the cuff member 25, at the point of use to snugly encase the region, limb, or digit of interest. As such, the sleeve 30" can have an unwrapped configuration with an open perimeter that can be substantially flat and a wrapped or attached configuration that provides the closed perimeter with an aperture sized to receive and overlie the targeted region and snugly conform to the underlying region (such as arm) of the patient. This type of sleeve 30" configuration may be particularly desirable for situations where a subject has an intravenous catheter inserted in his body that can make it difficult to slide the sleeve 30 into position onto the targeted sensor region.

Figure 13A:
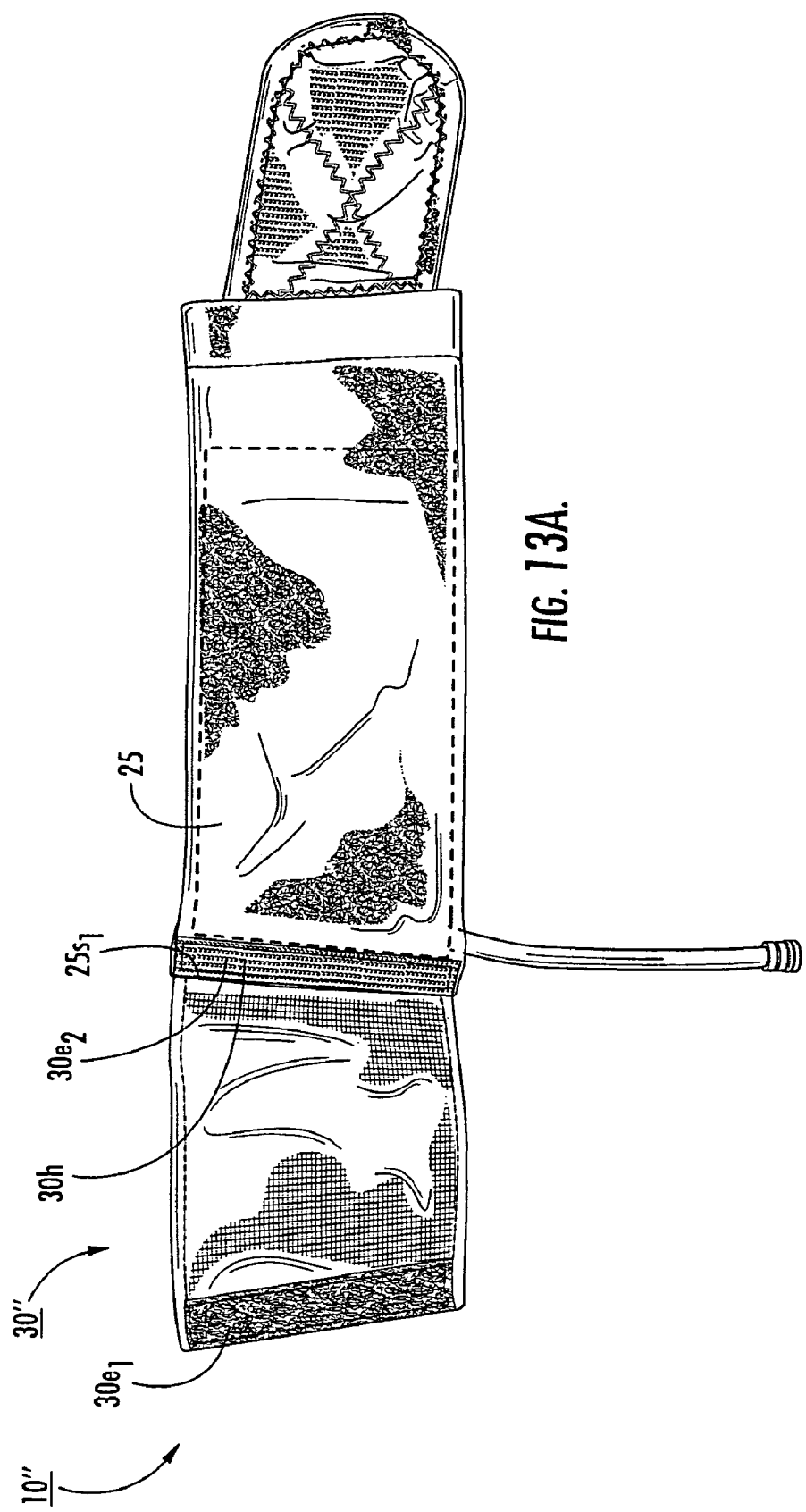
FIG. 13A is a front view of a cuff assembly having a sleeve that can be releaseably attached in situ on the patient according to embodiments of the present invention.

FIG. 13A illustrates a blood pressure cuff 10" with a sleeve 30" that has two opposing short edge portions $30e_1$, $30e_2$. In this embodiment, the second edge portion $30e_2$ is attached to the cuff member 25 at the cuff member edge portion $25s_1$ (either as an integrated or detachable component from the cuff member as described above). As such, the cuff member 25 can be configured with an attachment region $30h$ that engages with the sleeve first edge portion $30e_1$ as well as the second edge portion $30e_2$. To preserve the desired stretch size, sensor coupling and/or positioning features of the sleeve, the cuff member attachment region $30h$ may be configured to extend about a reduced size engagement region. For example, for VELCRO® loop and hook engagements, a small region of the mating hook and/or loop material may be provided on the edge portion $25s_1$ of the cuff member with a nylon or smooth material isolating the VELCRO® material and forcing a clinician to connect the member at small engagement space maintaining the correct size sleeve 30" for the patient by limiting the amount of adjustment in the sleeve size itself. The attachment means may be configured to reside on the outer or inner (shown) primary surface of the first short edge portion $30e_1$.

FIG. 13B illustrates that the sleeve first short edge portion $30e_1$ can be attached to its opposing end portion $30e_2$ proximate to the cuff member 25. The second end portion $30e_2$ can terminate into the cuff member 27. The second end portion $30e_2$ may be sewn or otherwise directly attached to the cuff member 25 at end portion $25s_1$. The sleeve second end portion $30e_2$ includes the attachment region $30h$ which is spaced proximate to but inwardly of the cuff member edge portion $25s_1$. As such, the sleeve 30" is configured to close upon itself.

Figure 13C:
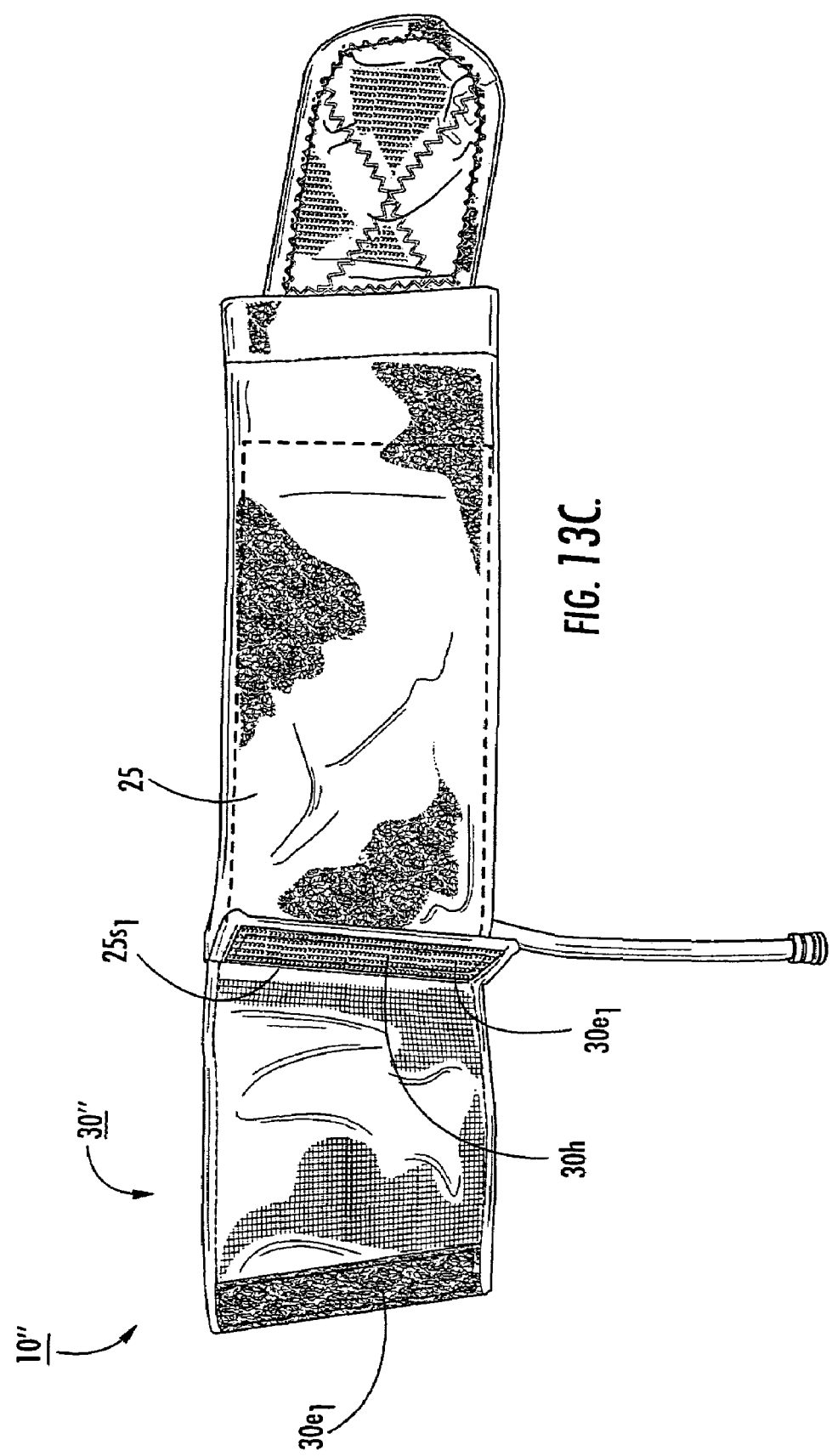
FIG. 13C is a front view of a cuff assembly having a sleeve that can be releaseably attached in situ on the patient according to embodiments of the present invention.

FIG. 13C illustrates an embodiment that also allows the sleeve 30" to close over itself similar to that shown in FIG. 13B. However, in this embodiment, the sleeve second end portion $30e_2$ extends a distance beyond the bounds of the cuff member 25 proximate the cuff member short edge portion $25s_1$. The sleeve extension holds the attachment region $30h$, again allowing the sleeve first short edge portion $30e_1$ to engage therewith. Instead of a sleeve extension length, the cuff member 25 may include an extension tab for engaging with the first edge portion $30e_1$ (not shown).

Figure 13D:
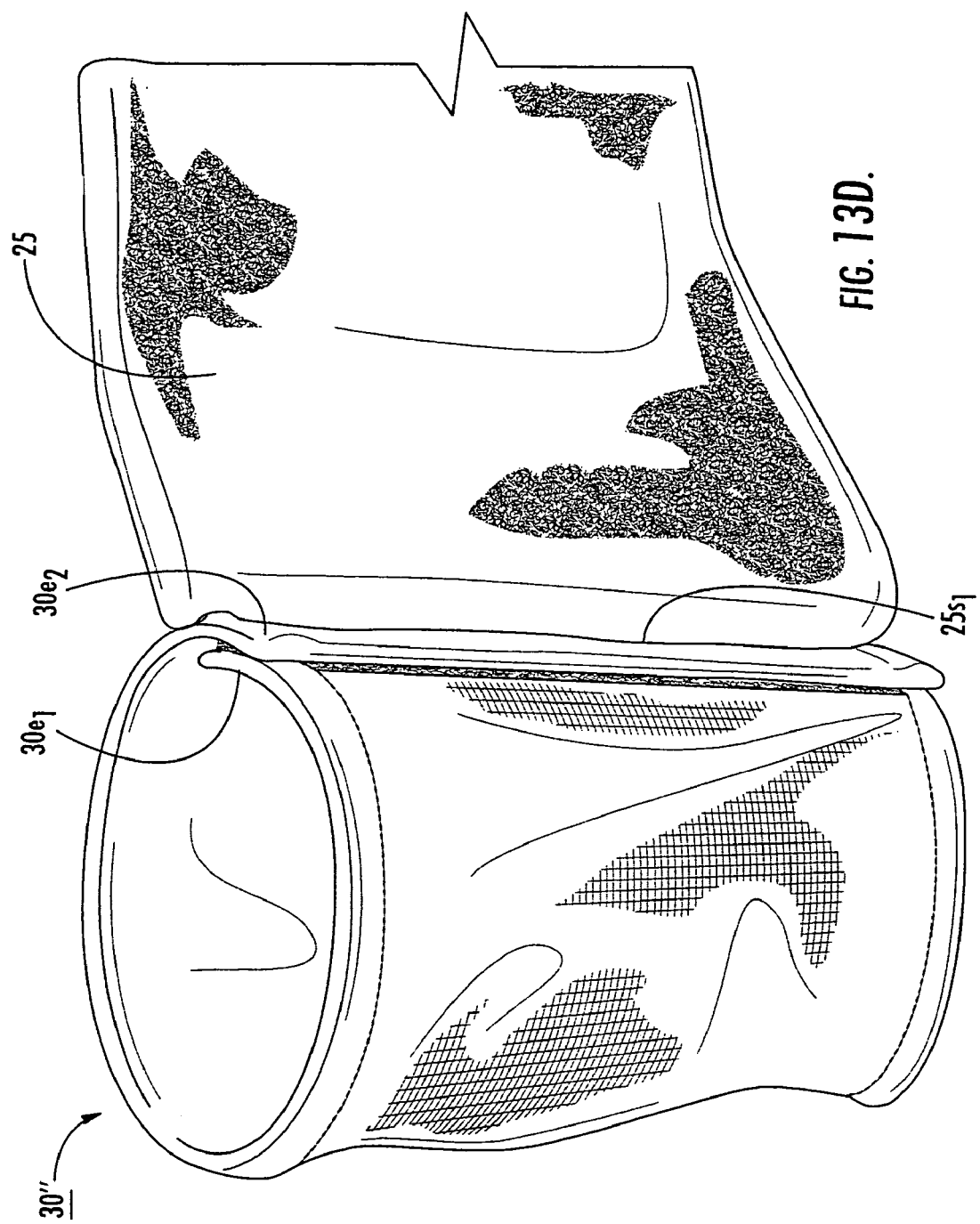
FIG. 13D is a perspective view of a sleeve member with portions that are releaseably attached together according to embodiments of the present invention.

FIG. 13D illustrates that in the wrapped releaseably attached configuration, the sleeve first edge portion $30e_1$ engages with the engagement region $30h$ (shown on the opposing end portion $30e_2$, but may be the cuff member end portion $25s_1$) so that the sleeve 30" presents a substantially flat overlying attachment zone.

As noted above, to provide the releaseably attachable wrapped or sleeve closed perimeter configuration, any suitable releaseably attachable engagement means can be used. For example, the sleeve 30" may again use hook and loop material such as VELCRO® for engagement to the sleeve and/or cuff member 25. As for other detachable configurations, pivot connectors, such as hooks and loops, locking tabs, spring loaded tabs, bayonet locks, zippers, adhesives, curable resin materials, or other suitable attachment means and/or devices, may also be used to provide the releaseable attachment interface between opposing short end portions $30e_2$, $30e_1$ of the sleeve 30" and/or the cuff member 25. The releaseable attachment should be formed with sufficient strength so as to be able to remain intact on the patient under the cuff member. However, the attachment strength can be less than that of the wrapped cuff member 25 itself as it is exposed to less tension and/or torsion during inflation and deflation of the inflatable cuff member 25. As such, for adhesive, resin, or other temporary bonds, the peel strength of the sleeve may be reduced relative to that of the cuff attachment strength.

In certain embodiments, such as those shown with the sleeve already pre-formed in to its closed perimeter shape prior to positioning on a patient, the sleeve 30 can facilitate installation by eliminating the need for a "D-ring" connector as well as permitting one-hand installation.

In addition, the sleeve 30 can inhibit the cuff member 25 from falling off the limb or sliding down the limb in ambulatory blood pressure (ABP) and/or stress testing applications (where more than one reading may be desired over a monitoring interval). For example, in ABP applications, a 12-24 hour monitoring period may be observed where the patient wears the cuff 10 for intermittent pressurization thereof. For conventional cuffs, repeated expansion and contraction of the cuff member 25 can loosen the cuff and allow the cuff member and/or the sensor to become incorrectly positioned or slip or fall from the limb (such as the arm). The sleeve 30 can reduce the likelihood that these operational difficulties will occur. The sleeve 30 can help keep the sensor 40 aligned with the desired arterial vessel and hold the senor 40 snugly against the limb or skin of the patient during inflation and/or deflation of the bladder.

It is also noted that the sleeve 30' can be used alone or as a separate component that resides under the wrapped cuff member 25.

FIGS. 9A-9G illustrate exemplary fabrication operations. As shown, the cuff assembly 10 may be formed by using five components: at least one sheet of sleeve fabric 30', a bladder pouch inner piece 25i (typically nylon), a bladder pouch outer piece 25o (typically VELCRO® loop material), a cuff tail 26, and a cuff tail cover 26c (typically formed of VELCRO® hook material).

FIG. 9B illustrates that the outer perimeter of the cuff tail cover 26c and cuff tail 26 can be serged and hemmed, leaving an angled edge 26e as a closure pocket. It is noted that other fabric finishing methods may be used as appropriate.

FIG. 9C illustrates the fabrication of the sleeve 30, 30' (shown with channel and chamber, 32, 31, respectively). In this embodiment, a unitary sheet of fabric 30s can be used without cutting the minor portion $30s_2$ of the fabric from the primary fabric body $30s_1$. This allows the lower edge 31e to be formed by folding the opposing sides of the material together, thereby permitting a seamless edge to form the sleeve 30'. The minor portion of the sheet $30s_1$ can be formed into a desired channel geometry (typically with a size that is sufficient to allow the minor portion of the sheet to form the outer perimeter of the channel to encase sewn corresponding lines on the primary body) and folded over the major portion $30s_2$.

In other embodiments, two separate material components may be used, one positioned to overlie the other and joined to define the associated chamber and channel 31, 32, as appropriate for the application. In this embodiment, the stretch fabric used to form the minor portion $30s_1$ of the sleeve 30' may formed of the same material, or may be formed be of a different material blend or fabric than the major portion $30s_2$. The lower edge of the chamber 31 may be formed to be open or closed as noted above. The perimeter edges of the sleeve fabric 30s may be serged with thread about the perimeter of the fabric and the edges can be hemmed. The shape of the sensor channel 32 and chamber 31 can be sewn and the ends tied to inhibit loosening of the stitching during use. A stretch stitch can be used to form the sensor chamber 31 and channel 32 and the threads used to attach/define channel 32 and sensor chamber 31 and serged edges can be elastic. The stretch stitch can be selected so that it provides a stretch capacity that is substantially equivalent to the stretch of the material.

To assemble, the sensor 40 with cable 42 can be slid into the channel 32 exit port 32e and directed through the channel 32 so that the sensor 40 resides at the sensor chamber 31. In other (open edge 31e') embodiments, the sensor 40 can be threaded into the channel 32 and chamber 31 from the bottom of the sleeve 30' (not shown).

Figure 9D:
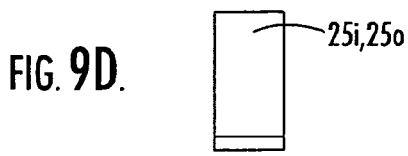
FIG. 9D illustrates an elongated bladder pouch for an inflatable bladder member corresponding to one of the components shown in FIG. 9A according to embodiments of the present invention.
Figure 9E:
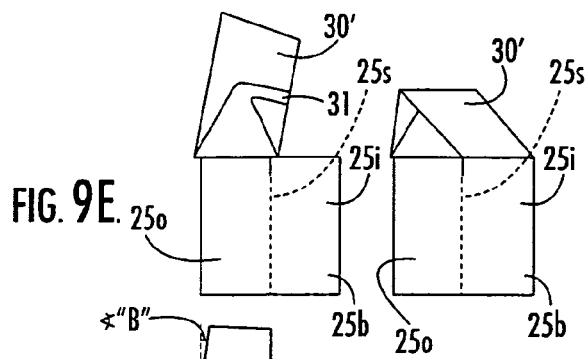
FIG. 9E illustrates that the partially formed sleeve of FIG. 9C can be attached to the bladder pouch of FIG. 9D according to embodiments of the present invention.
Figure 9F:
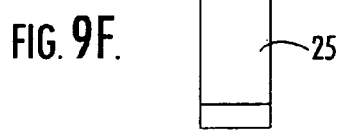
FIG. 9F illustrates that after the components shown in FIG. 9E are attached, the bladder pouch can be folded and secured to form an enclosed bladder pouch with an attached sleeve according to embodiments of the present invention.
Figure 9G:
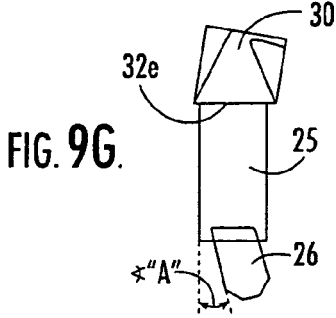
FIG. 9G illustrates that the completed cuff assembly with the cuff tail and cuff tail cover of FIG. 9B attached to the sleeve and pouch of FIG. 9F according to embodiments of the present invention.

FIG. 9D illustrates that the bladder pouch components 25i, 25o can be hemmed and FIG. 9E illustrates the two bladder pouch components 25i, 25o can be joined, typically hemmed, together so that they have a center seam 25s extending between the two components parallel to the opposing long edges to form a body 25b. FIG. 9E also shows that one short edge portion of the sleeve 30' can be attached to a first (short) side of the joined pouch body and the opposing short (lateral) side of the sleeve 30' can be joined to the other side of the bladder pouch body 25b, taking care to leave the channel exit port 32e open. The cuff member or bladder pouch body 25b can then be folded and joined together to form the desired end configuration to hold the inflatable bladder 27 therein. The tail 26 can be attached to the bladder pouch 25 as shown in FIG. 9G. The tail 26 can be configured so that about 1 inch of VELCRO® material is exposed on the inside of the pouch to allow the bladder pouch 25p to be closed to hold the bladder 27 therein. The tail 26 may be configured to extend from the cuff member 25 at a downwardly extending angle "A" of about 15 degrees from the long edges of the cuff member 25. Similarly, as shown in FIG. 9F, the sleeve 30' may be configured to extend in a downwardly extending angle "B" relative to the long edges of the cuff member 25. Angle "B" may be between about 525 degrees, and may typically be about 15 degrees.

The inflatable bladder 27 is typically formed of a non-latex material and can be sized to correspond to the patient size contemplated by each cuff member 25. For example, nylon and polyurethane layers that can be RF welded and configured to withstand about 300 mm Hg or 6 psi. The inflation tube 28 may be configured to have an inner diameter of about ⅛ inch.

Figure 11:
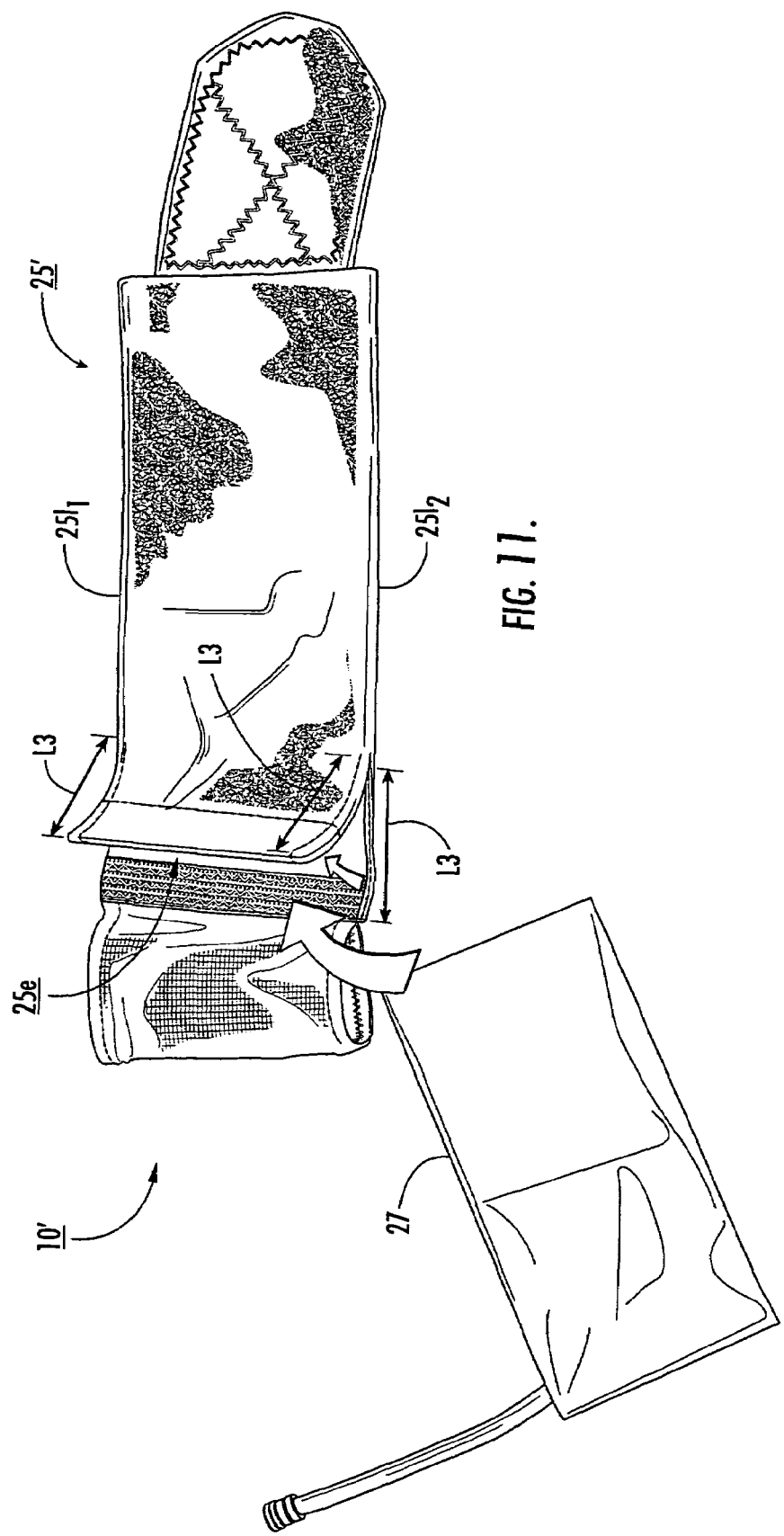
FIG. 11 is a front view of a cuff assembly according to embodiments of the present invention.
Figure 12A:
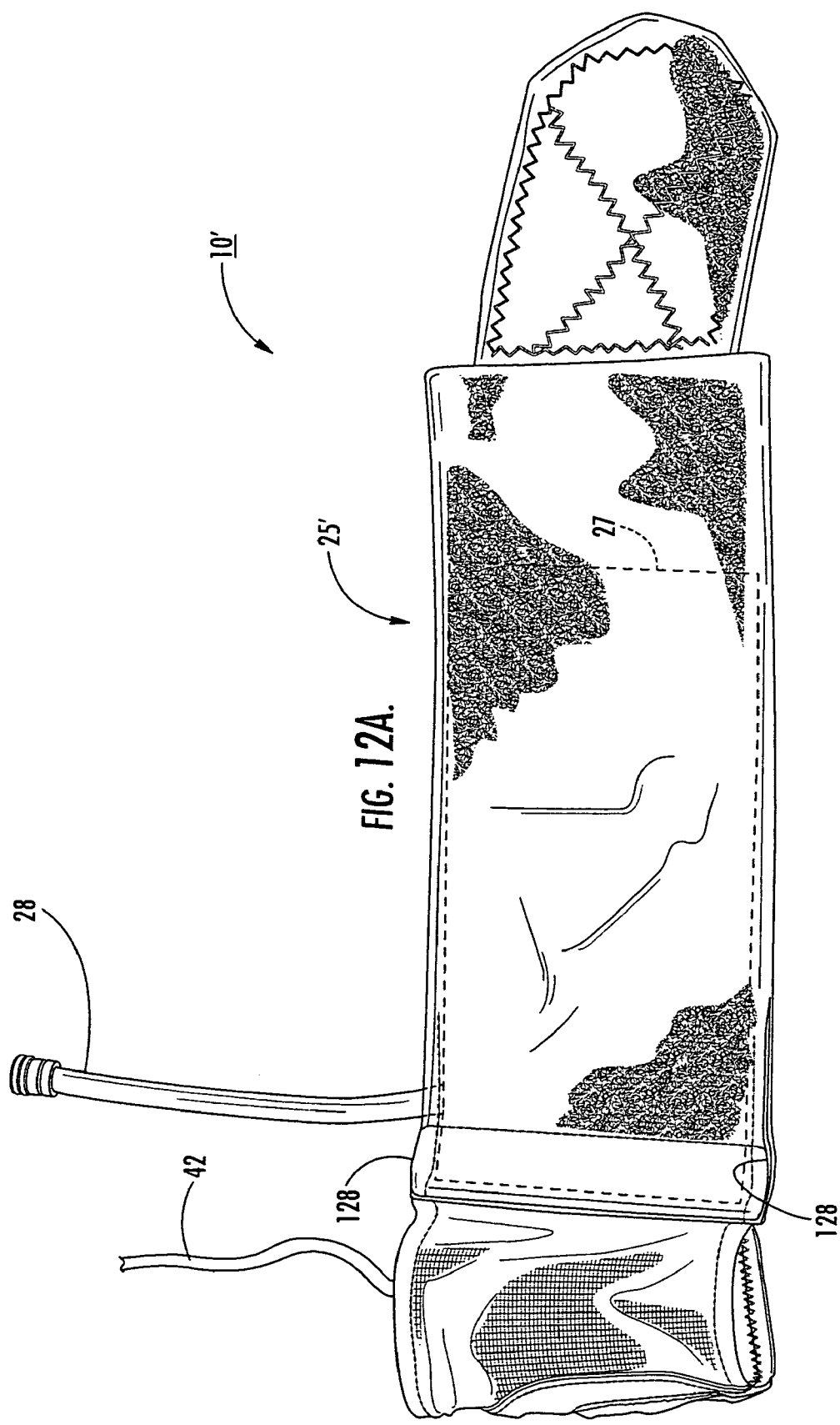
FIG. 12A is a front view of the cuff assembly shown in FIG. 11 with the bladder in position in the cuff and the tube exiting the cuff according to embodiments of the present invention.
Figure 12B:
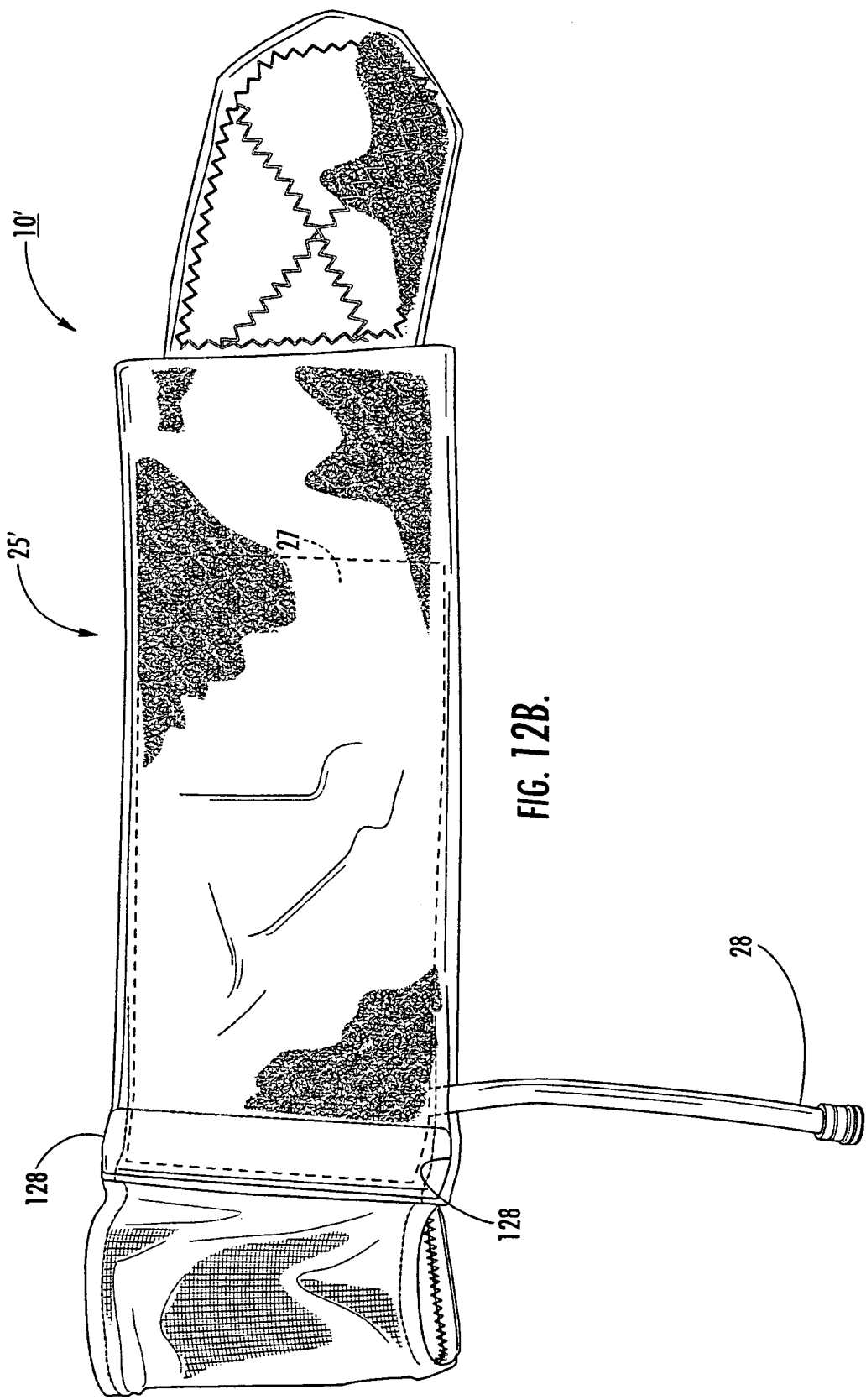
FIG. 12B is a front view of the cuff assembly shown in FIG. 11 with the bladder in position in the cuff and the tube exiting the cuff in a direction that is different from that shown in FIG. 12A according to alternate embodiments of the present invention.

FIGS. 11 and 12A-12B illustrate an alternative embodiment of the cuff assembly 10' with a corresponding cuff member 25'. In this embodiment, the cuff member 25' is configured with a bladder entry port 25e (configured to allow the bladder 27 to be inserted into the cuff member 25') at the end portion that opposes the tail portion 26. In the embodiment shown, the bladder entry port 25e is configured to be at the same short end portion $25s_1$ as the sleeve 30. As shown, the bladder entry port 25e has releaseably detachable overlying primary surfaces at the short edge portion $25s_1$. The attachment configuration can be VELCRO® or any of the releaseably engageable attachment means described above. In addition, one or both of the opposing long edges $25l_1$, $25l_2$, proximate the bladder port entry 25e is open a length $L_3$ that is sufficient to allow the inflation tube 28 of the bladder 27 to reside within the opening 128 defined by the opposing open edge portions when the port 25e is closed and the bladder 27 is in position in the cuff member 25' (FIGS. 12A, 12B). The bladder 27 is easily inserted into the cuff member 25' with the inflation tube 28 extending out of the desired long edge portion (upper or lower, $25l_1$, $25l_2$, respectively) and then the port 25e closed by pressing the overlying material together to hold the bladder 27 therein. As shown, where the cuff member 25' may be configured so that a clinician or user can orient the bladder in the pouch of the cuff member 25' at the point of use to direct the inflation tube to extend upwardly or downwardly simply by inserting the bladder 27 into the cuff member 25' in the appropriate direction. Generally, for longer duration monitoring, the tube 28 will be oriented to exit upwardly out of the cuff member 25' (reducing the interference with movement of the arm or leg). Further, the cuff member 25' (as for the cuff member 25 described above), can be used for either left or right limbs or arms.

As shown in FIG. 12A, the tube 28 and the sensor line 42 can both be configured to extend upwardly out of the cuff 10', leaving the arm of the user substantially free from hanging wires or tubes. FIG. 12B illustrates that the tube can be directed to extend downwardly out of the cuff 10'.

The cuff member 25 may be imprinted, adorned, embossed or otherwise provided with directions on use and/or or alignment indicia to allow for operator reference and proper positioning of the cuff member 25 and/or sensor 40 in the sleeve 30, 30'. For example, as shown in FIG. 6, the sleeve 30' may include an alignment arrow 40A positioned on the sleeve 30' over the sensor 40 and pointing to where the sensor 40 should be relative to the underlying artery (for example, the brachial artery in the arm). The alignment may be presented in a visually accentuated manner, such as in color, bold, or alignment symbol used to provide the indicia. Alternatively, an arrow or other indicia may be placed away from the sensor chamber 31 to indicate a center alignment position of the sleeve 30, 30', 30" with the arm or other body portion. As the sleeve 30, 30', 30" can be positioned prior to closing the cuff 10 with the sensor 40 held securely in position, more reliable positioning may be achieved using the cuff assemblies 10 contemplated by the present invention.

Figure 10:
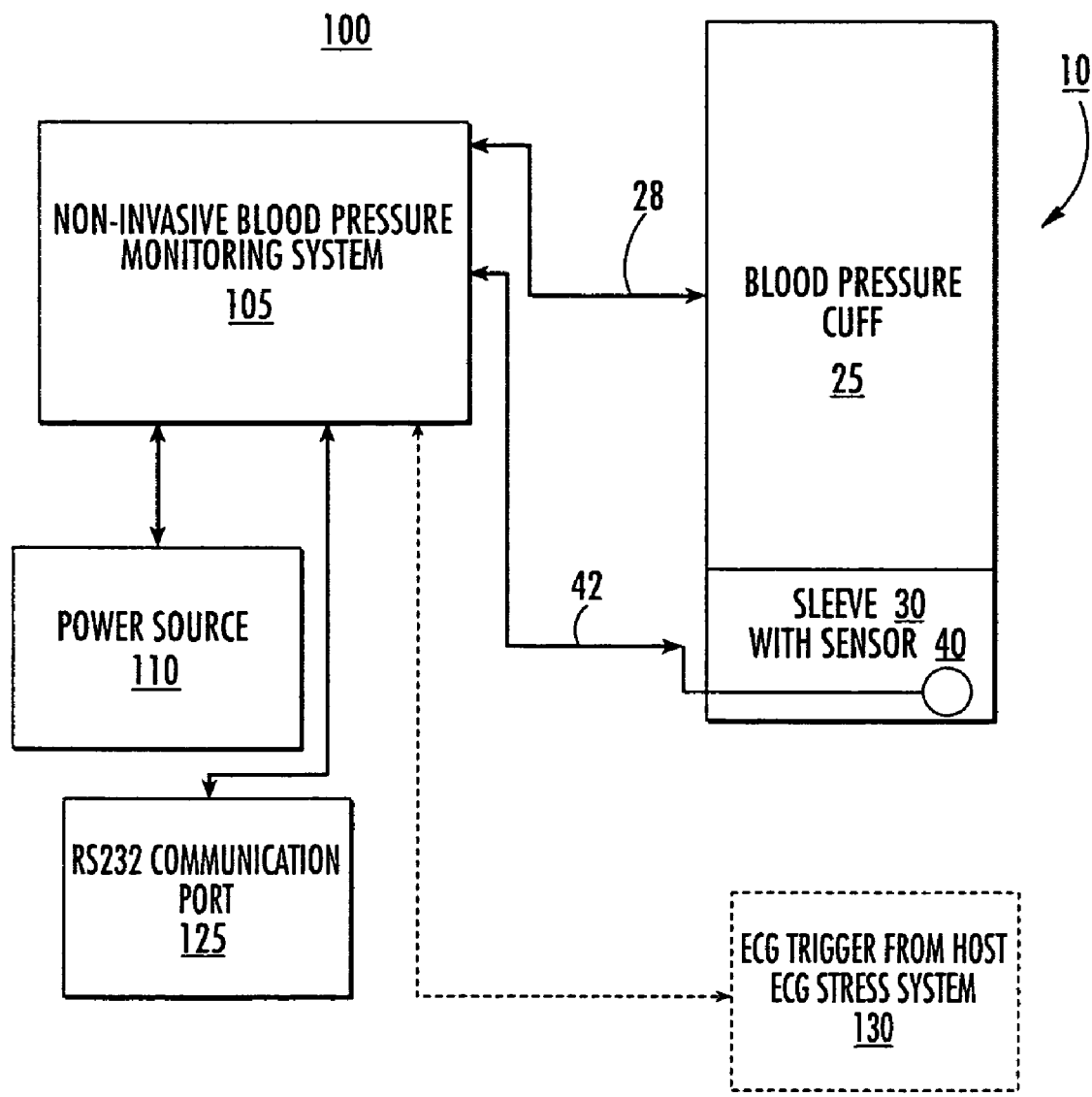
FIG. 10 is a schematic diagram of an automated blood pressure monitoring system according to embodiments of the present invention.

FIG. 10 illustrates one embodiment of a blood pressure monitoring system 100 in communication with a power source 110 (DC, such as a 9 or 12V battery, or AC) and an RS232 communication port 125 that allows for bi-directional communications from external, remote, and/or host or separate computer systems. The RS232 port 125 may be configured to as a peripheral device that can interface directly with other testing evaluation systems, such as ECG stress systems. The RS232 port 125 is optional and control may be carried out by the system 100 itself, independent of other systems, and readings may be displayed locally on the monitoring system 105 itself. The monitoring system 105 can include a series of valves and a pump that allows the cuff 25 to be inflated to a pressure above systolic to occlude the artery, then slowly deflated beyond diastolic so that the systolic and diastolic pressures can be determined. The system 100 may include pressure relief valves to prevent over-inflation and warning or alert systems for abnormal unit operation, sensor misplacement, and/or at-risk patient measurement values. The system 100 may include noise filtering circuits and computer program code to reduce noise in the obtained or monitored signal (such as may occur with a patient undergoing tread mill activity).

Thus, the blood pressure monitoring system 100 may be configured to allow interaction between a test site (that may have access to a cardiologist or other specialist) and one or a plurality of remote ("local") patient sites for telemedicine applications. The measurements can be obtained and relayed from the through the use of a computer network. The computer network can be an intranet (computers connected within a particular organization, company, coalition, or group), or the Internet (such as a global computer network, i.e., the world wide web).

The system 100 may be ambulatory or stationary. The system 100 includes the blood pressure cuff assembly 10 described above with its inflation tube 28 and sensor cable 42 connected to an automated non-invasive blood pressure monitoring system 105. The monitoring system 105 can include a controller, such as digital signal processor, and application programs that direct the acquisition and output of blood pressure measurements. The system 105 may be a stand-alone unit or be adapted to operate and interface with other monitoring systems, such as a host system that may include ECG triggers from a host ECG Stress System. The system 105 may also include a display monitor (not shown).

In certain embodiments, the automated blood pressure monitoring system 100 can include a plurality of inflatable blood pressure cuff assemblies, each sized and configured to accommodate different ranges of patient sizes. Each cuff assembly 10 includes an elongate cuff member 25 having opposing long edges and opposing short edge portions with an inflatable fluid chamber 27 therein and a resilient sleeve 30 having a predetermined patient size range that is attached to a respective one of the opposing short edge portions of the inflatable elongate cuff member 25. The system 100 also includes a unit that inflates the desired blood pressure cuff to a pressure sufficient to restrict blood flow in a selected artery of a patient proximate the sleeve and the blood pressure cuff (such as via a pump and valving connected to the tube 28 to inflate the bladder or cuff as is well known to those of skill in the art). The system also includes control units for controllably (sufficiently slowly) releasing the inflation pressure in the blood pressure cuff (also employing known devices such as controllers, pressure sensors, valves, restrictor plates, flow meters, and the like), and devices for detecting a signal corresponding to blood pressure measurements of the patient (whether by Korotkoff-sound "K-sound", mercurial or pneumatic manometer, or other appropriate sensing technique).

Figure 14:
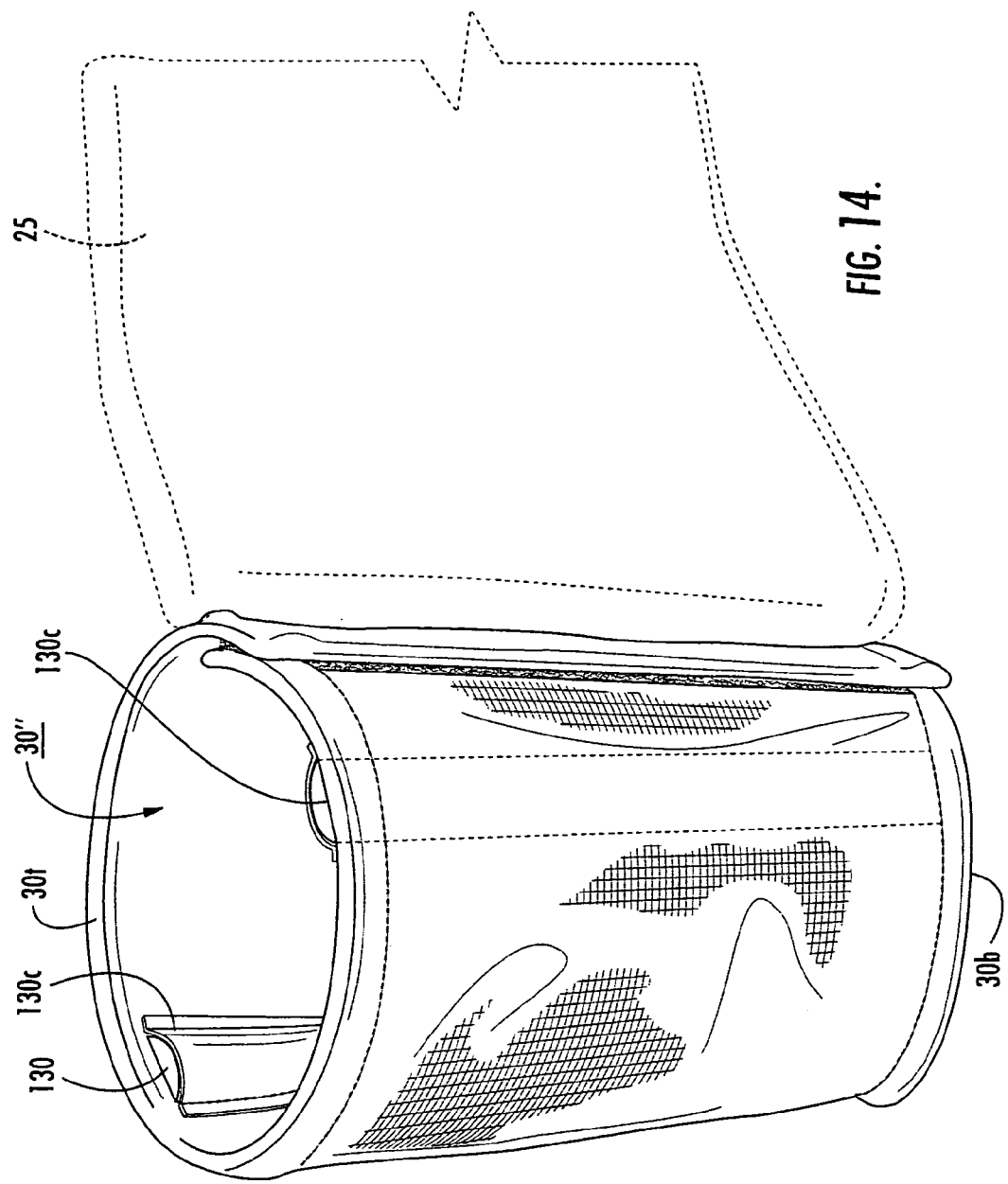
FIG. 14 is a perspective view of a cuff assembly having a sleeve member with rib supports according to embodiments of the present invention.

FIG. 14 illustrates another embodiments of a cuff assembly 10 with a sleeve 30''' similar to that shown in FIG. 13D, but having spaced apart rib support members 130, each held in a respective rib channel 130c. FIG. 15 illustrates a cuff assembly 10 similar to that shown in FIG. 11, but with a sleeve 30''' having one rib support member 130 and a corresponding rib channel 130c.

As shown in FIGS. 16A and 16B, the rib support member(s) 130 can be configured with a flexible resilient body that flexes and substantially conforms to the contour of the arm of the user in position while having sufficient structural rigidity so that, in position, the upper portion of the sleeve 30''' will be inhibited from rolling down. The rib support member(s) 130 can comprise a polymer material such as polystyrene, a metal (typically with a polymer coating), a fabric, a laminated structure, or other suitable material. The rib support member 130 may be substantially planar and have a substantially planar profile as shown in FIGS. 15 and 17A, or may have a curvilinear profile as shown in FIGS. 14 and 17B. The planar member 130 may be a thin body (typically less than bout 5 mm thick, and more typically about 3 mm or less).

In particular embodiments, the rib support member 130 may have a semicircular profile as shown in FIG. 17B. The member 130 may have a thickness that is about 5 mm or less. The planar portion of the rib support member 130 may be oriented to face the sleeve 30''' as shown in FIG. 15 or oriented to face the arm of the user (not shown). FIG. 17C illustrates that the rib support member 130 may have an upper edge portion that has laterally extending arms 130L (such as an "I" or "T" configuration). In position in the sleeve 30''', the center elongate portion 130p extends longitudinally (up and down) while the arms extend substantially orthogonally laterally. The end portions of the rib support members 130e (and/or the channel 130C) may be configured to inhibit pinching or other patient discomfort may be configured to provide the cushion/softness. FIG. 17D illustrates that the rib support member 130 can include encapsulated end portions 131 which may be formed using caps or overmolded edges of a polymer material (such as silicone) with a softness that cushions a user from discomfort associated with contact with the rib support member 130. Other rib member 130 configurations may also be used, including circular profile (cylindrical body) configurations and the like.

In other embodiments, the sleeve 30''' may include at least one rib support member 130 of a stretchable fabric having an increased structural rigidity relative to the remaining portions of the sleeve (not shown). The stretchable fabric rib support may be sewn over an underlying portion of the sleeve or seamed into the sleeve (not shown).

The rib support member(s) 130 may be configured with an elongate body to extend a predetermined length down from the upper edge portion of the sleeve 30'''. Typically, the rib support member 130 is configured to extend greater than about a major portion of the length of the sleeve 30''' and more typically, substantially the entire length of the sleeve 30''' as shown in FIGS. 14 and 15. As shown, in particular embodiments, the rib support member(s) 130 can terminate proximate the upper and lower edge portions of the sleeve 30''' so that the rib support member(s) 130 does not extend beyond the boundary of the sleeve 30'''. The rib support members 130 may be placed in the rib channels 131 formed in the sleeve as shown in FIGS. 14 and 15, or directly attached via adhesive, laminating, fusing, stitching and the like. Also, although shown as placed to the inside of the sleeve 30''', the rib support member(s) 130 may be positioned on the outside or at an intermediate location within the sleeve.

When used with a sleeve 30' having a sensor channel 31 as shown in FIG. 4, the rib support member 130 can be positioned so as not to interfere with the sensor channel and operation. FIG. 14 illustrates that the sleeve 30''' can include two rib support members 130. As shown, the rib support members 130 may be substantially diametrically opposed from each other. FIG. 15 illustrates that the sleeve 30''' can include a single rib support member 130. The single support member 130 may be positioned so that on a user, the rib support member is at an outer arm location or about an arm location that does not overlay the sensing location. Other sleeve configurations, number of rib support members, and alternate rib configurations can also be used.

The sleeve 30''' with rib support member(s) 130 may be particularly suitable for large patients having sleeve sizes of 32-44 cm or greater, typically greater than 44 cm (such as sleeves sized at 44-60 cm or greater) and/or patients having soft folds of arm tissue (decreased muscle tone or firmness). In certain embodiments, the ribbed sleeve 30''' may be provided only for L, XL and/or XXL size patients in a kit of assorted sleeve sizes. The ribbed sleeve 30''' may also be particularly suitable for longer evaluations, such as ABP testing.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An inflatable blood pressure cuff assembly comprising:
an inflatable elongate cuff member having opposing long edges and opposing short edge portions with an inflatable fluid chamber therein; and
a resilient sleeve attached to a respective one of the opposing short edge portions of the inflatable elongate cuff member, wherein the sleeve comprises at least one substantially longitudinally extending rib support member, wherein the sleeve has a body sized and configured to elastically expand to snugly and substantially conformably fit on a limb of a patient prior to inflation of the cuff member whereby the at least one rib is configured to inhibit the sleeve from rolling up and/or down the limb of the patient, wherein, in position, the cuff defines a first closed member and the sleeve defines a second closed member that resides inside the first closed member, attached to the cuff, and wherein the sleeve is adapted to elastically expand about the body portion of the user in a form fitting manner before inflation of the cuff member and elastically compress against the body portion when the cuff member is inflated.

2. A blood pressure cuff assembly according to claim 1, wherein the at least one rib support member has an elongate flexible body configured to inhibit an upper edge portion of the sleeve from rolling down when in position on a user.

3. A blood pressure cuff assembly according to claim 1, wherein the sleeve comprises at least one rib channel sized and configured to hold the at least one rib support member therein.

4. A blood pressure cuff assembly according to claim 1, wherein the at least one rib support member is a plurality of laterally spaced apart rib support members configured to inhibit an upper edge portion of the sleeve from rolling down when in position on a user.

5. A blood pressure cuff assembly according to claim 1, wherein the sleeve is air permeable and comprises a fabric that includes stretch fibers.

6. A blood pressure cuff assembly according to claim 1, wherein the sleeve has a closed perimeter configuration defining an aperture extending in the axial direction, wherein the sleeve aperture is sized and configured to stretch to receive a limb of a patient therein during use.

7. A blood pressure cuff assembly according to claim 6, wherein the sleeve aperture has a first configuration with a first width during periods of non-use and a second configuration with an expanded second width when in position on a patient, wherein, in the second configuration, the sleeve is substantially conformable to and is configured to reside securely against a desired portion of the limb of the patient with sufficient compressive force so that it is able to maintain its desired longitudinal position to thereby inhibit slippage during use.

8. A blood pressure cuff assembly according to claim 5, wherein the sleeve comprises nylon fibers.

9. A blood pressure cuff assembly according to claim 5, wherein the sleeve comprises spandex fibers.

10. A blood pressure cuff assembly according to claim 5, wherein the sleeve has opposing upper and lower edge portions, and wherein, in position on a patient, the sleeve is configured to have an elastic lateral stretch of at least about 15% at the lower edge portion to provide the second configuration width.

11. A blood pressure cuff assembly according to claim 10, wherein the sleeve is configured to accommodate patients having limbs that vary in width by up to at least about 150%.

12. A blood pressure cuff assembly according to claim 11, wherein the sleeve is sized and configured to accommodate patients having limbs that vary in width between about 100-205%.

13. A blood pressure cuff assembly according to claim 1, wherein the sleeve has a frustoconical shape.

14. A blood pressure cuff assembly according to claim 1, wherein the cuff member is bladderless.

15. A blood pressure cuff assembly according to claim 1, wherein the cuff member comprises a pouch and an inflatable bladder that is configured to reside therein.

16. A blood pressure cuff assembly according to claim 15, wherein the sleeve is formed of a fabric comprising nylon as a major constituent and spandex as a minor constituent.

17. A blood pressure cuff assembly according to claim 1, wherein, in position, the sleeve is configured to define a first closed member before the cuff member is wrapped over the sleeve and the cuff member defines a second closed member after the cuff member is wrapped over the sleeve, and wherein the sleeve comprises a sensor chamber.

18. A blood pressure cuff assembly according to claim 17, wherein the sleeve comprises a sensor held in the sensor chamber.

19. A blood pressure cuff assembly according to claim 17, wherein the sleeve comprises upper and lower edge portions, and wherein the sensor chamber is located proximate the lower edge portion.

20. A blood pressure cuff assembly according to claim 19, wherein the sleeve sensor chamber has a lower edge portion that is seamless.

21. A blood pressure cuff assembly according to claim 19, wherein the sleeve further comprises a cable channel in communication with the sensor chamber.

22. A blood pressure cuff assembly according to claim 21, wherein the sleeve cable channel is curvilinear.

23. A blood pressure cuff assembly according to claim 1, wherein the sleeve has opposing first and second short end portions, and wherein the first end portion is configured to releaseably attach to the cuff member and/or the second short end portion of the sleeve.

24. A blood pressure cuff assembly according to claim 1, wherein the cuff member and sleeve are configured to accommodate both the left and right arms of patients.

25. A blood pressure cuff assembly according to claim 1, wherein the assembly is configured for ambulatory blood pressure measurements.

26. A blood pressure cuff assembly according to claim 1, wherein the sleeve is formed of an anisotropic material.

27. A blood pressure cuff assembly according to claim 1, wherein the sleeve is attached to the cuff member in a releasably detachable manner, and is configured to reside against the limb of the patient with the cuff wrapped thereabout during use.

28. A blood pressure cuff assembly according to claim 1, wherein the assembly is configured for stress test blood pressure measurements.

29. A blood pressure cuff assembly according to claim 1, wherein the sleeve is fixedly attached to the cuff member.

30. A blood pressure cuff assembly according to claim 1, wherein the at least one rib is configured to project inwardly toward skin of the limb of the patient inside the wrapped cuff.

31. An inflatable blood pressure cuff assembly comprising:
an inflatable elongate cuff member having opposing long edges and opposing short edge portions with an inflatable fluid chamber therein; and
a resilient sleeve attached to a respective one of the opposing short edge portions of the inflatable elongate cuff member, wherein the sleeve comprises at least one rib support member,
wherein the sleeve comprises upper and lower edge portions, and wherein a sensor chamber is located proximate the lower edge portion, wherein the sleeve sensor chamber has a lower edge portion that is seamless, and
wherein the sleeve sensor chamber has a lower edge portion that is open.

32. An inflatable blood pressure cuff assembly comprising:
an inflatable elongate cuff member having opposing long edges and opposing short edge portions with a fluid chamber therein, in operation, the short edge portions being configured to wrap about a body portion of a user and connect to each other; and
a resilient sleeve configured to reside under the wrapped cuff member attached to a single one of the short edge portions and extending outwardly from a primary surface of the cuff, wherein the sleeve comprises at least one substantially axially extending rib support member, and wherein at least a major portion of the sleeve is configured to elastically expand to snugly and substantially conformably fit on a limb of a patient.

33. A blood pressure cuff assembly according to claim 32, wherein the at least one rib is configured to project inwardly toward skin of the limb of the patient inside the wrapped cuff.

34. A blood pressure cuff assembly according to claim 32, wherein, in position, the sleeve is configured to define a first closed member before the cuff member is wrapped over the sleeve and the cuff member defines a second closed member after the cuff member is wrapped over the sleeve.

35. A blood pressure cuff assembly according to claim 32, wherein the at least one rib support member has an elongate flexible body configured to inhibit an upper edge portion of the sleeve from rolling down when in position on a user.

36. A blood pressure cuff assembly according to claim 32, wherein the sleeve is configured with at least one rib channel sized and configured to hold the at least one rib support member therein.

37. A blood pressure cuff assembly according to claim 32, wherein the at least one rib support member is a plurality of laterally spaced apart rib support members configured to inhibit an upper edge portion of the sleeve from rolling down when in position on a user.

38. A blood pressure cuff assembly according to claim 32, wherein the sleeve remains unattached to the cuff member during operation.

39. A blood pressure cuff assembly according to claim 32, wherein the sleeve is releasably attachable to one of the short edge portions of the elongate cuff member.

40. A blood pressure cuff assembly according to claim 32, wherein the sleeve is fixedly attached to the elongate cuff member.

41. A blood pressure cuff assembly according to claim 32, wherein the sleeve includes opposing first and second short end portions, and wherein the first end portion is configured to releaseably attach to the cuff member and/or the sleeve second end portion.

42. An inflatable blood pressure cuff assembly comprising:
an inflatable elongate cuff member having opposing long edges and opposing short edge portions with an inflatable fluid chamber therein; and
a resilient sleeve attached to a respective one of the opposing short edge portions of the inflatable elongate cuff member, wherein the sleeve comprises at least one rib support member,
wherein the sleeve comprises upper and lower edge portions, and wherein a sensor chamber is located proximate the lower edge portion,
wherein the sleeve further comprises a curvilinear cable channel in communication with the sensor chamber,
wherein the sleeve cable channel includes an intermediate segment that is arcuate, a lower first segment that is substantially longitudinal, and an upper segment above the arcuate segment that includes lateral directional components.

43. A blood pressure cuff assembly according to claim 42, further comprising a sensor and a cable attached to the sensor, wherein the sensor is held proximate a lower portion of the sleeve and the cable is directed to travel through the channel and exit the cuff assembly proximate an upper portion of the sleeve.

44. A blood pressure cuff assembly according to claim 43, wherein the sleeve is configured as a single-use disposable member.

45. An automated blood pressure monitoring system, comprising:
a plurality of inflatable blood pressure cuff assemblies, each sized and configured to accommodate a different patient size range, each cuff assembly comprising an elongate cuff member having opposing long edges and opposing short edge portions with an inflatable fluid chamber therein and a resilient sleeve having a predetermined patient size range that is attachable and/or attached to a respective one of the opposing short edge portions of the inflatable elongate cuff member, wherein the sleeve comprises at least one substantially axially extending rib support member, and wherein the sleeve has a body sized and configured to elastically expand to snugly and substantially conformably fit on a limb of a patient prior to closing the cuff member about the limb of the patient whereby the at least one rib is configured to inhibit the sleeve from rolling up and/or down the limb of the patient, wherein, in position, the cuff defines a first closed member and the sleeve defines a second closed member that resides inside the first closed member, attached to the cuff, and wherein the sleeve is adapted to elastically expand about the body portion of the user in a form fitting manner before inflation of the cuff member and elastically compress against the body portion when the cuff member is inflated;
an inflation unit in fluid communication with a selected one of the blood pressure cuffs and configured to generate a pressure sufficient to restrict blood flow in a selected artery of a patient proximate the sleeve and the blood pressure cuff;
means for releasing the inflation pressure in the blood pressure cuff; and
means for detecting a signal corresponding to blood pressure measurements of the patient.

46. A system according to claim 45, wherein the sleeves are releasably attached to the cuff members.

47. A system according to claim 46, wherein one short edge portion is configured to be releaseably attachable to the other opposing sleeve short edge portion and/or the cuff member to define a closed sleeve having an axially extending aperture.

48. A system according to claim 45, wherein the at least one rib support member has an elongate flexible body configured to inhibit an upper edge portion of the sleeve from rolling down when in position on a user.

49. A system according to claim 45, wherein the sleeve comprises at least one rib channel sized and configured to hold the at least one rib support member therein.

50. A system according to claim 49, wherein the at least one rib support member is a plurality of laterally spaced apart rib support members configured to inhibit an upper edge portion of the sleeve from rolling down when in position on a user.

51. A system according to claim 45, further comprising a kit of replacement sleeves that are configured to be individually selectably releaseably attachable to the blood pressure cuff members.

52. A system according to claim 51, wherein the sleeves are arranged in different predetermined sizes and are configured to be disposable single-use sleeves.

53. A system according to claim 45, wherein the system is an ambulatory blood pressure measurement system.

54. A system according to claim 45, wherein the system is a stress test blood pressure measurement system.

55. A system according to claim 45, wherein the sleeves are fixedly attached to the corresponding cuff members.

56. A system according to claim 45, wherein the at least one rib is configured to project inwardly toward skin of the limb of the patient inside the wrapped cuff.

* * * * *

UNITED STATES PATENT AND TRADEMARK OFFICE
CERTIFICATE OF CORRECTION

| | | |
|---|---|---|
| PATENT NO. | : 7,311,670 B2 | Page 1 of 1 |
| APPLICATION NO. | : 10/705364 | |
| DATED | : December 25, 2007 | |
| INVENTOR(S) | : Just et al. | |

It is certified that error appears in the above-identified patent and that said Letters Patent is hereby corrected as shown below:

Column 19, Claim 11, Line 5: Please correct "the sleeve is configured to"
To read -- the sleeve elastically stretches to --

Signed and Sealed this

Sixth Day of May, 2008

JON W. DUDAS
*Director of the United States Patent and Trademark Office*